United States Patent
Liu et al.

(10) Patent No.: US 12,062,198 B2
(45) Date of Patent: Aug. 13, 2024

(54) METHOD AND SYSTEM FOR MULTI-MODALITY JOINT ANALYSIS OF VASCULAR IMAGES

(71) Applicant: SHENZHEN KEYA MEDICAL TECHNOLOGY CORPORATION, Shenzhen (CN)

(72) Inventors: Shubao Liu, College Park, MD (US); Junjie Bai, Seattle, WA (US); Youbing Yin, Kenmore, WA (US); Feng Gao, Seattle, WA (US); Yue Pan, Seattle, WA (US); Qi Song, Seattle, WA (US)

(73) Assignee: SHENZHEN KEYA MEDICAL TECHNOLOGY CORPORATION, Shenzhen (CN)

( * ) Notice: Subject to any disclaimer, the term of this patent is extended or adjusted under 35 U.S.C. 154(b) by 241 days.

(21) Appl. No.: 17/723,863

(22) Filed: Apr. 19, 2022

(65) Prior Publication Data
US 2023/0095242 A1  Mar. 30, 2023

Related U.S. Application Data

(60) Provisional application No. 63/249,002, filed on Sep. 27, 2021.

(51) Int. Cl.
*G06T 7/33* (2017.01)
*A61B 6/00* (2006.01)
(Continued)

(52) U.S. Cl.
CPC ............ *G06T 7/344* (2017.01); *A61B 6/5247* (2013.01); *A61B 8/5261* (2013.01);
(Continued)

(58) Field of Classification Search
CPC ......... G06T 7/344; G06T 7/0012; G06T 7/75; G06T 11/00; G06T 17/00; G06T 19/20; G06T 2207/10081; G06T 2207/10088; G06T 2207/10101; G06T 2207/10132; G06T 2207/20221; G06T 2207/30096;
(Continued)

(56) References Cited

U.S. PATENT DOCUMENTS

2016/0307331 A1* 10/2016 Mollus ................. G16H 30/40
2019/0362855 A1* 11/2019 Ma ....................... G06T 7/0016
(Continued)

*Primary Examiner* — Chong Wu
(74) *Attorney, Agent, or Firm* — Bayes PLLC

(57) ABSTRACT

Embodiments of the disclosure provide methods and systems for multi-modality joint analysis of a plurality of vascular images. The exemplary system may include a communication interface configured to receive the plurality of vascular images acquired using a plurality of imaging modalities. The system may further include at least one processor, configured to extract a plurality of vessel models for a vessel of interest from the plurality of vascular images. The plurality of vessel models are associated with the plurality of imaging modalities, respectively. The at least one processor is also configured to fuse the plurality of vessel models associated with the plurality of imaging modalities to generate a fused model for the vessel of interest. The at least one processor is further configured to provide a diagnostic analysis result based on the fused model of the vessel of interest.

20 Claims, 14 Drawing Sheets

(51) Int. Cl.

| | |
|---|---|
| *A61B 8/08* | (2006.01) |
| *G06T 7/00* | (2017.01) |
| *G06T 7/73* | (2017.01) |
| *G06T 11/00* | (2006.01) |
| *G06T 17/00* | (2006.01) |
| *G06T 19/20* | (2011.01) |
| *A61B 5/00* | (2006.01) |
| *A61B 5/055* | (2006.01) |
| *A61B 6/03* | (2006.01) |
| *A61B 8/12* | (2006.01) |

(52) U.S. Cl.
CPC .............. G06T 7/0012 (2013.01); G06T 7/75 (2017.01); G06T 11/00 (2013.01); G06T 17/00 (2013.01); G06T 19/20 (2013.01); *A61B 5/0066* (2013.01); *A61B 5/055* (2013.01); *A61B 6/032* (2013.01); *A61B 8/12* (2013.01); *G06T 2207/10081* (2013.01); *G06T 2207/10088* (2013.01); *G06T 2207/10101* (2013.01); *G06T 2207/10132* (2013.01); *G06T 2207/20221* (2013.01); *G06T 2207/30096* (2013.01); *G06T 2207/30101* (2013.01); *G06T 2210/41* (2013.01); *G06T 2219/2004* (2013.01)

(58) Field of Classification Search
CPC ....... G06T 2207/30101; G06T 2210/41; G06T 2219/2004; A61B 6/5247; A61B 8/5261; A61B 5/0066; A61B 5/055; A61B 6/032; A61B 8/12

See application file for complete search history.

(56) References Cited

U.S. PATENT DOCUMENTS

2021/0137634 A1* 5/2021 Lang ...................... A61B 5/113
2023/0397816 A1* 12/2023 Forneris ................. G16H 30/40

* cited by examiner

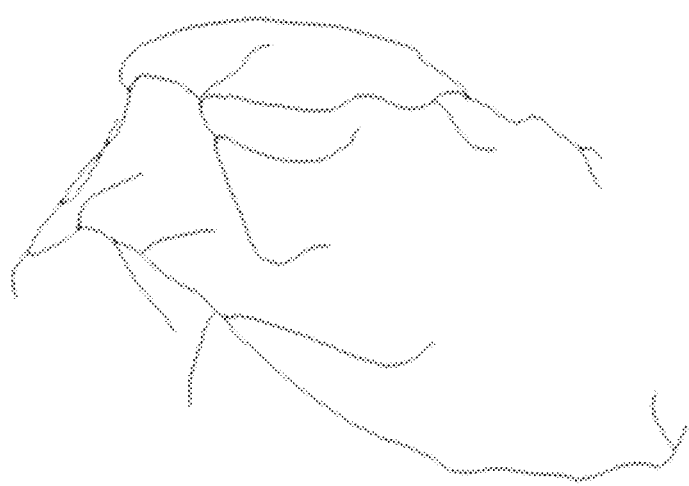
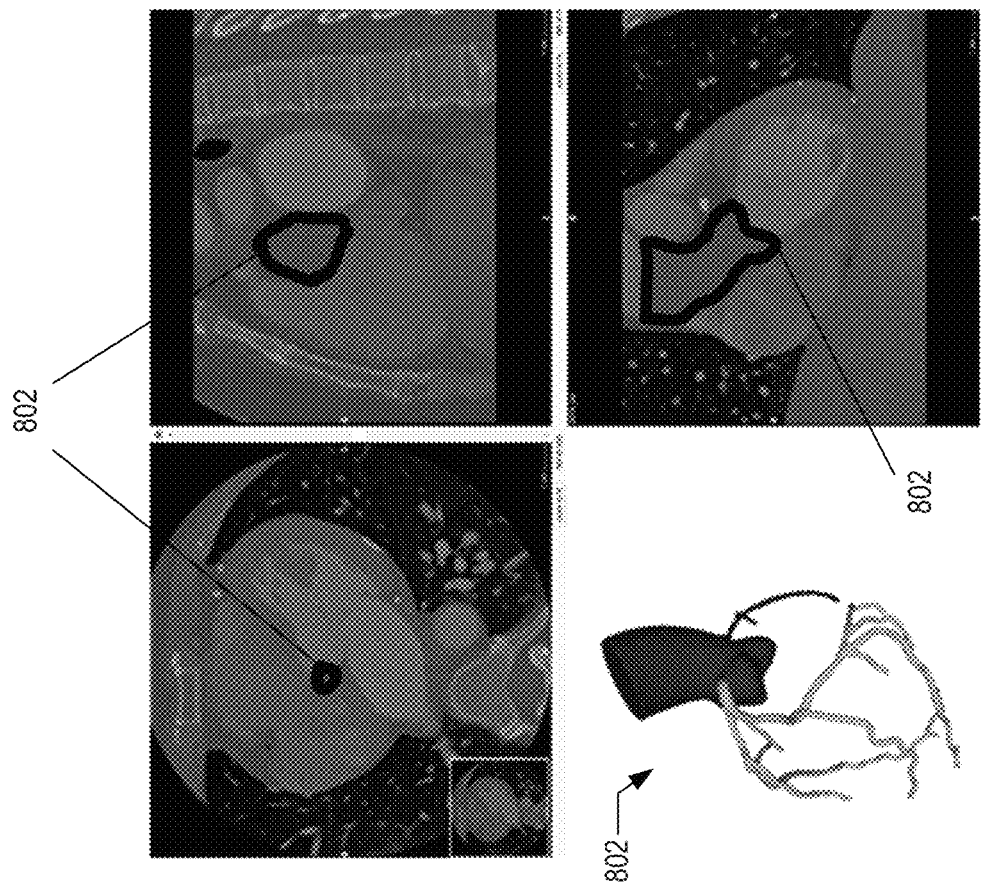
Figure 8B
Figure 8A

METHOD AND SYSTEM FOR MULTI-MODALITY JOINT ANALYSIS OF VASCULAR IMAGES

CROSS-REFERENCE TO RELATED APPLICATIONS

This application claims the benefit of priority to U.S. Provisional Application No. 63/249,002, filed on Sep. 27, 2021, the entire content of which is incorporated herein by reference.

TECHNICAL FIELD

The present disclosure relates to methods and systems for processing vascular images, and more particularly to methods and systems for jointly processing and analyzing vascular images acquired using a plurality of imaging modalities.

BACKGROUND

Vascular diseases are a leading cause of death globally, in which coronary artery diseases are the most common type. Motivated by an increasing need to comprehensively assess the anatomy and function of an artery, different imaging modalities have been developed to aid in the diagnosis and treatment of artery diseases. For example, invasive X-ray Angiography (XA), 3D angiography (such as Computed Tomography Angiography (CTA), Magnetic Resonance Angiography (MRA), etc.), and intravascular imaging (such as Optical Coherence Tomography (OCT), Intravascular Ultrasound (IVUS), etc.) are widely used for the diagnosis of artery diseases. These imaging modalities can provide different and complementary information for assessing the artery.

For example, 3D angiography (e.g., CTA, MRA) produces a 3D volumetric image (or 3D-plus-time (4D) dynamic images) to show a vessel tree, such as a coronary, carotid or cerebral vessel in 3D (or 4D) with a moderate resolution (~0.5 mm). For example, CTA is a non-invasive imaging tool that uses a Computerized Tomography (CT) scanner to image blood vessels with injection of contrast material to highlight the blood vessels from other issues. However, due to limitation of the CT scanning, calcium deposit (a common type of artery lesion) appears with blooming artifact, which makes it challenging to identify real boundary of the lesion.

In another example, invasive XA is an invasive diagnostic procedure that inserts a catheter into a blood vessel (such as an artery) to administer contrast material and taking 2D X-ray projection images of the blood vessel with a higher resolution than CTA. For example, X-ray images of the transient contrast material that flows inside the coronary artery allow visualization of artery lumen through which the blood flows. Coronary angiography is the golden standard to visualize coronary artery stenosis (i.e., the narrowing of the blood vessel). However. 2D XA only shows the artery lumen through which the blood flows, and lesions which cause the narrowing of the lumen are not visible in the 2D X-ray images. In addition, the 2D projection of the invasive XA may produce artifacts such as fore-shortening and occlusion of the blood vessel.

In yet another example, intravascular imaging techniques including IVUS and OCT provide detailed vessel lumen and wall information with high resolution. A specially designed catheter attached with a miniaturized ultrasound probe (for IVUS) or an ultra-infrared light source (for OCT) is used to traverse inside a vessel segment, and then, the intravascular imaging techniques can generate a series of 2D cross-sectional image frames in the vessel segment with a high resolution. Due to different physics characteristics of the ultrasound and the ultra-infrared light, OCT provides a higher resolution than IVUS, with sharp boundary and tissue type information in a smaller field of view than IVUS, whereas IVUS provides a larger field of view showing a more complete picture of lesions even at locations farther away from the vessel lumen. However, such intravascular imaging techniques usually provide images for each vessel path separately. In addition, various artifacts caused by guidewire, blood, stents, etc., are often observed in the images.

Thus, the available imaging modalities for capturing vascular images have their respective advantages and problems. Embodiments of the disclosure take advantage of the benefits and address the problems of the different imaging modalities by jointly analyzing vascular images acquired using different imaging modalities to thoroughly evaluate a vessel of interest. In embodiments of the disclosure, advantages of the different imaging modalities can be combined and enlarged whereas the problems of the different imaging modalities can be minimized or overcome, which is beneficial for the assessment of the vessel of interest as well as diagnosis and treatment of potential vessel diseases.

SUMMARY

Embodiments of methods and systems for processing vascular images, and more particularly, for jointly processing and analyzing vascular images acquired using a plurality of imaging modalities, are disclosed.

In one aspect, embodiments of the disclosure provide a system for multi-modality joint analysis of a plurality of vascular images. The exemplary system may include a communication interface configured to receive the plurality of vascular images acquired using a plurality of imaging modalities. The system may further include at least one processor, configured to extract a plurality of vessel models for a vessel of interest from the plurality of vascular images. The plurality of vessel models are associated with the plurality of imaging modalities, respectively. The at least one processor is also configured to fuse the plurality of vessel models associated with the plurality of imaging modalities to generate a fused model for the vessel of interest. The at least one processor is further configured to provide a diagnostic analysis result based on the fused model of the vessel of interest.

In another aspect, embodiments of the disclosure also provide a method for multi-modality joint analysis of a plurality of vascular images. The exemplary method may include receiving, at a communication interface, the plurality of vascular images acquired using a plurality of imaging modalities. The method may also include extracting, by at least one processor, a plurality of vessel models for a vessel of interest from the plurality of vascular images. The plurality of vessel models are associated with the plurality of imaging modalities, respectively. The method may further include fusing, by the at least one processor, the plurality of vessel models associated with the plurality of imaging modalities to generate a fused model for the vessel of interest. The method may additionally include providing, by the at least one processor, a diagnostic analysis result based on the fused model of the vessel of interest.

In yet another aspect, embodiments of the disclosure further provide a non-transitory computer-readable medium having a computer program stored thereon. The computer program, when executed by at least one processor, performs a method for multi-modality joint analysis of a plurality of vascular images. The exemplary method may include receiving the plurality of vascular images acquired using a plurality of imaging modalities. The method may also include extracting a plurality of vessel models for a vessel of interest from the plurality of vascular images. The plurality of vessel models are associated with the plurality of imaging modalities, respectively. The method may further include fusing the plurality of vessel models associated with the plurality of imaging modalities to generate a fused model for the vessel of interest. The method may additionally include providing a diagnostic analysis result based on the fused model of the vessel of interest.

It is to be understood that both the foregoing general description and the following detailed description are exemplary and explanatory only and are not restrictive of the invention, as claimed.

BRIEF DESCRIPTION OF THE DRAWINGS

FIGS. 8A-8B are graphical representations illustrating exemplary CTA vessel segmentation and 3D centerline extraction, according to certain embodiments of the disclosure.

DETAILED DESCRIPTION

Reference will now be made in detail to the exemplary embodiments, examples of which are illustrated in the accompanying drawings.

Figure 1A:
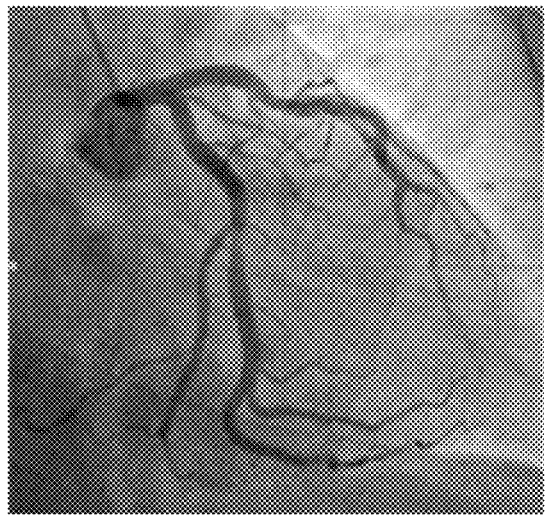
FIGS. 1A-1D illustrate exemplary vascular ages acquired with a plurality of imaging modalities, according to certain embodiments of the disclosure.
Figure 1B:
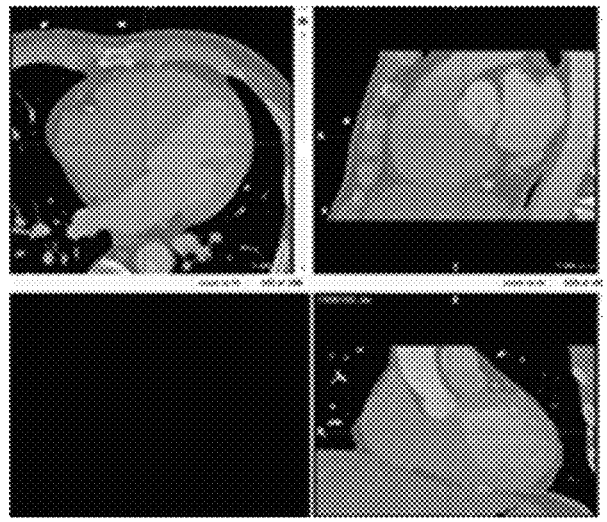
Figure 1C:
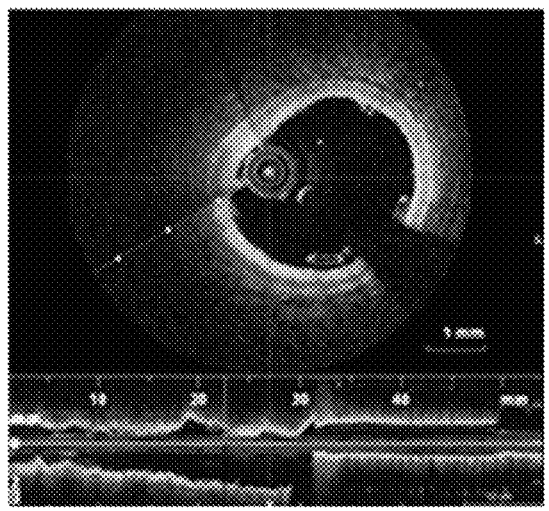
Figure 1D:
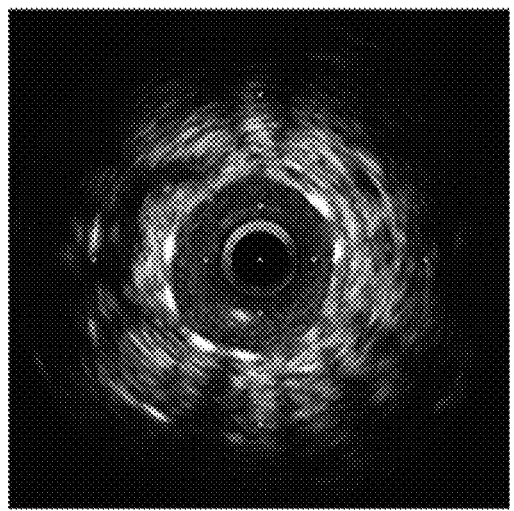

FIGS. 1A-1D illustrate exemplary vascular images acquired by a plurality of imaging modalities, according to certain embodiments of the disclosure. For example, FIG. 1A shows an exemplary vascular image acquired using the XA (referred to as XA image hereinafter), which is a 2D projection image depicting a vessel tree with a plurality of vessel branches. FIG. 1B shows an exemplary vascular image acquired using CTA (referred to as CTA image hereinafter), which includes 3D volumetric vessel data. FIG. 1C shows an exemplary vascular image from an image sequence acquired using OCT (referred to as OCT image hereinafter), which is a 2D cross-sectional image depicting detail lumen and wall information of a vessel. FIG. 1D shows an exemplary vascular image acquired using IVUS (referred to as IVUS image hereinafter), which is also a 2D cross-sectional image depicting detail lumen and wall information of a vessel.

Consistent with the disclosure herein, the terms "picture," "image," "frame," and "image frame" may be used interchangeably and may refer to a vascular image captured using a particular imaging modality. The vascular image can include a vessel of interest. In some embodiments, the vascular image can be an image frame from a sequence of image frames in a video recorded using the particular imaging modality.

Consistent with the disclosure herein, systems and methods for multi-modality joint analysis of vascular images are disclosed. The systems and methods can jointly analyze vascular images (such as those depicted in FIGS. 1A-1D) acquired using different imaging modalities to thoroughly evaluate a vessel of interest. For example, the systems and methods disclosed herein can extract a plurality of vessel models for a vessel of interest from a plurality of vascular images. The plurality of vessel models are associated with a plurality of imaging modalities, respectively. Each vessel model may include at least one of a centerline, a radius, or a segmentation mask, etc., of the vessel of interest for a corresponding imaging modality. The systems and methods disclosed herein can fuse the plurality of vessel models to generate a fused model for the vessel of interest. Then, the systems and methods disclosed herein can provide a diagnostic analysis result based on the fused model of the vessel of interest.

Consistent with the disclosure herein, the systems and methods disclosed herein can reduce ambiguity and improve accuracy of disease diagnosis associated with the vessel of interest. The comparison and fusion of vessel models derived from multiple imaging modalities can benefit the interpretation and assessment of a vessel disease. Vessel and lesion characteristics can be assessed and compared from the fused model generated based on the vascular images acquired using the multiple imaging modalities.

example, the systems and methods disclosed herein can combine or fuse (1) a first vessel model for a vessel of interest derived from OCT images and (2) a second vessel model for the same vessel of interest derived from CTA images by leveraging the detailed lesion characteristics shown in the OCT images and the complete and intuitive 3D shape from the CTA images. Then, a precise 3D fused model can be generated thereof. Thus, the systems and methods disclosed herein can enable detailed diagnosis of lesion in the precise 3D fused model because the 3D fused model can provide accurate vessel information with detailed lesion types and/or characteristics. The 3D fused model can be used to correct diagnosis of ambiguous (or missed) lesion regions on the CTA images. For example, observations from the OCT images are transferred onto a 3D CTA model generated from the CTA images to derive the 3D fused model with a precise overall shape of the vessel and accurate lesion localization and classification of the vessel.

In another example, the systems and methods disclosed herein can combine or fuse a first vessel model derived from CTA images and a second vessel model derived from XA images to generate a fused model by leveraging the accurate 3D shape from the CTA images and the accurate lumen boundary from the XA images. Thus, the systems and methods disclosed herein can provide improved vessel reconstruction quality in both centerline and radius estimation, especially in a stenosis region.

Consistent with the disclosure herein, the systems and methods disclosed herein can further establish ground-truth for different imaging modalities to aid later model trainings. For example, a vessel model of a vessel of interest derived from OCT images can provide ground-truth verification of calcification for the vessel of interest, which can be mapped to vessel models derived from other imaging modalities (e CTA, MRA) to serve as training data for calcification detection and segmentation in the other imaging modalities.

Consistent with the disclosure herein, the systems and methods disclosed herein can build a holistic understanding on vessel structures and vessel diseases quantitively before, during and/or after an intervention or surgery procedure. Specifically, XA images capture blood flow information of the vessel, while suffering from the occlusion and foreshortening issues. CTA images capture a global 3D structure of the vessel accurately, while having a relatively lower resolution in fine details of the vessel lumen and wall. OCT captures high resolution OCT images of the vessel lumen and wall structure. By processing and combining the images captured using different imaging modalities, a holistic understanding on the structure and function of the vessel can be built. Thus, the systems and methods disclosed herein can help doctors to plan, evaluate, and perform treatments before, during and/or after the intervention or surgery procedure.

For example, CTA can be used for disease screening and treatment planning before the intervention or surgery procedure since it is a non-invasive imaging modality. During the intervention or surgery procedure, invasive XA or intravascular imaging techniques can be used to further assess the disease. By jointly processing the noninvasive CTA images and the invasively-acquired images using the XA or intravascular imaging techniques, the systems and methods disclosed herein can provide doctors with an entire vessel structure together with local detailed lesion information. After the intervention or surgery procedure, noninvasive procedures can be used again for follow-up evaluation of the disease.

Consistent with the disclosure herein, the systems and methods disclosed herein can provide an improved fused model for performing functional analysis from the joint analysis of vascular images acquired using different imaging modalities. The functional analysis may include, for example, evaluation of fractional flow reserve (FFR), evaluation of instantaneous Wave-free Ratio (iFR), etc., of the vessel of interest. Compared to a vessel model built from a single imaging modality, the fused model built from these imaging modalities is a more comprehensive vessel model. The fused model may include vessel information including, e.g., a vessel tree structure, a blood flow speed, a stenosis location and degree, a lesion size, lesion characteristics, etc., and can be used for the functional analysis for the vessel of interest.

Consistent with the disclosure herein, the systems and methods disclosed herein can help doctors to visualize an artery structure and any artery diseases comprehensively through the fused model, which enables immersive visualization and operation in augmented and/or virtual reality. For example, while intravascular imaging provides most detailed lesion information, it can be hard to put the vascular images acquired using intravascular imaging back into a 3D perspective with all the bifurcations. However, CTA or XA images can provide valuable context about the overall vessel tree shape, so that bifurcations from the CTA or XA images can be intuitively mapped to the bifurcations from the vascular images acquired using intravascular imaging. Thus, a combination of the vascular images acquired using intravascular imaging with the CTA or XA images can provide a better visualization and understanding of the artery structure and disease lesions.

Figure 2:
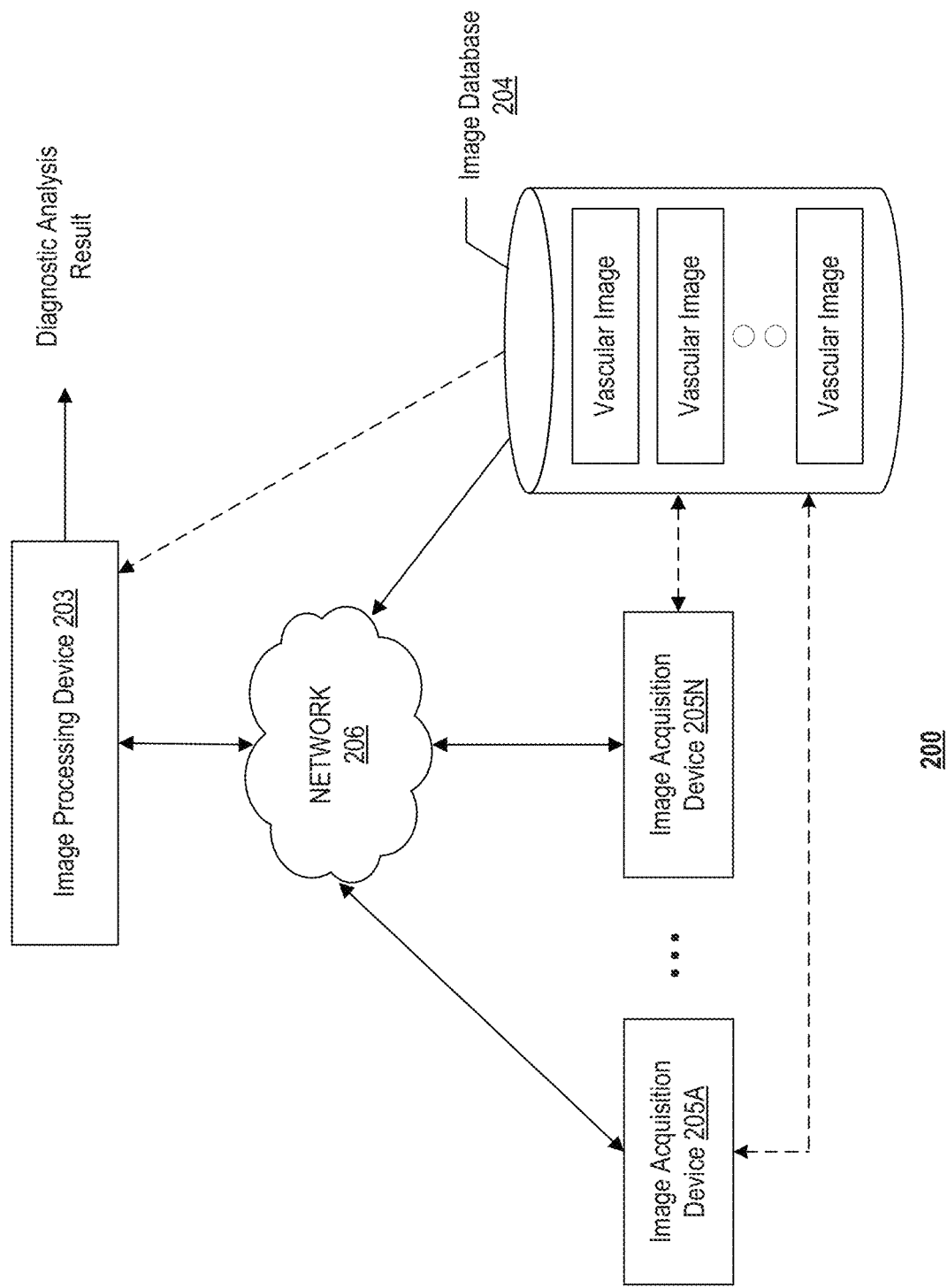
FIG. 2 illustrates a schematic diagram of an exemplary diagnostic image analysis system, according to certain embodiments of the disclosure.

FIG. 2 illustrates an exemplary diagnostic image analysis system 200, according to some embodiments of the present disclosure. Consistent with the present disclosure, diagnostic image analysis system 200 may be configured to analyze vascular images acquired by a plurality of image acquisition devices 205A, . . . , 205N (also referred to as image acquisition device 205, individually or collectively) and perform a diagnostic analysis based on the image analysis. In some embodiments, image acquisition device 205 may be a CT scanner that acquires 2D or 3D CT images. Image acquisition device 205 may be used to perform a CT angiography test. For example, image acquisition device 205 may be a 3D multi-detector row CT scanner for volumetric CT scans. In some embodiments, image acquisition device 205 may use one or more other imaging modalities, including, e.g., MRA, Magnetic Resonance imaging (MRI), functional MRI (e.g., fMRI, DCE-MRI and diffusion MRI), Positron Emission Tomography (PET), Single-Photon Emission Computed Tomography (SPECT), XA, Optical Coherence Tomography (OCT), fluorescence imaging, ultrasound imaging (e.g., IVUS), radiotherapy portal imaging, or the like.

In some embodiments, image acquisition device 205 may capture vascular images including a blood vessel (e.g., a whole vessel tree or one or more vessel branches). In some embodiments, each volumetric CT exam may include 20~1094 CT slices with a slice-thickness varying from 0.25 mm to 5 mm. The reconstructed image may have 512×512 pixels with in-plane pixel spatial resolution from 0.29×0.29 $mm^2$ to 0.98×0.98 $mm^2$.

As shown in FIG. 2, diagnostic image analysis system 200 may include an image processing device 203 and an image database 204. In some embodiments, diagnostic image analysis system 200 may include more or less of the components shown in FIG. 2. Diagnostic image analysis system 200 may optionally include a network 206 to facilitate the communication among the various components of diagnostic image analysis system 200, such as database 204, devices 203 and 205. For example, network 206 may be a local area network (LAN), a wireless network, a cloud computing environment (e.g., software as a service, platform as a service, infrastructure as a service), a client-server, a wide area network (WAN), etc. In some embodiments, network 206 may be replaced by wired data communication systems or devices. For example, image acquisition device 205 and image processing device 203 may be coupled to image database 204 directly without network 206 (illustrated as dashed lines in FIG. 2).

In some embodiments, the various components of diagnostic image analysis system 200 may be remote from each other or in different locations, and be connected through network 206 as shown in FIG. 2. In some alternative embodiments, certain components of diagnostic image analysis system 200 may be located on the same site or inside one device. For example, image database 204 may be located on-site with or be part of image processing device 203. As another example, image acquisition device 205 and image processing device 203 may be components of the same computer or processing device.

Image processing device 203 may include a processor and a non-transitory computer-readable medium (discussed in detail in connection with FIG. 3). The processor may perform instructions of a medical diagnostic image analysis program stored in the medium. Image processing device 203 may additionally include input and output interfaces (discussed in detail in connection with FIG. 3) to communicate with image database 204, network 206, and/or a user interface (not shown). The user interface may be used for selecting vascular images for analysis, initiating the analysis process, displaying the diagnostic results, or the like.

Image processing device 203 may communicate with image database 204 to receive vascular images. In some embodiments, the vascular images stored in image database 204 may include 2D or 3D (or even higher dimensional) images (e.g., 2D or 3D cardiac CT images) from one or more underlying subjects (e.g., patients susceptible to heart diseases). The vascular images may be acquired by image acquisition devices 205. For example, the vascular images may include one or more of XA images, MRA images, CTA images, OCT images, IVUS images, etc. Image processing device 203 is further described below in more detail with reference to FIGS. 3-15.

Figure 3:
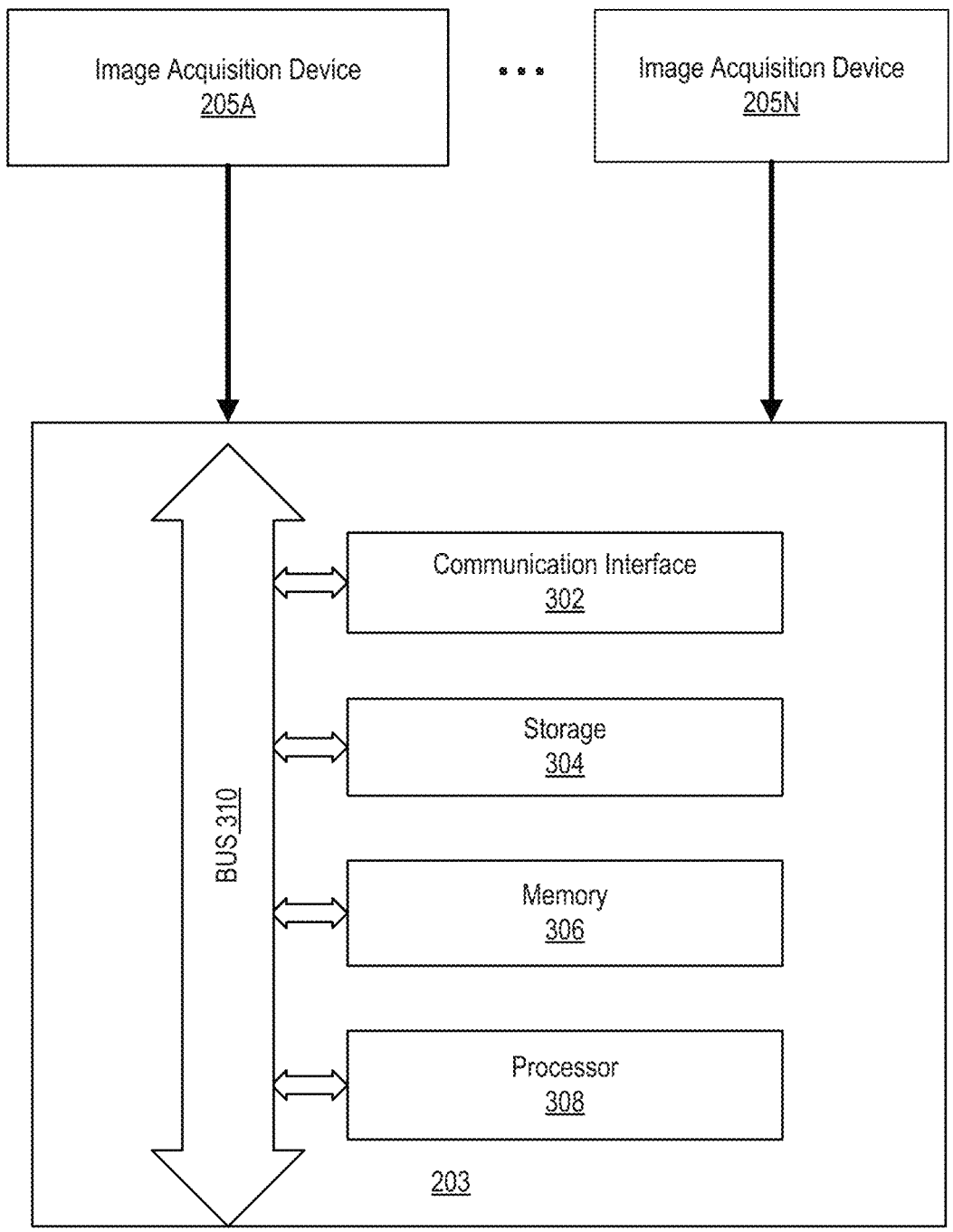
FIG. 3 illustrates a schematic diagram of an exemplary image processing device, according to certain embodiments of the disclosure.

Systems and methods of the present disclosure may be implemented using a computer system, such as one shown in FIG. 3. In some embodiments, image processing device 203 may be a dedicated device or a general-purpose device. For example, image processing device 203 may be a computer customized for a hospital for processing image data acquisition and image data processing tasks, or a server in a cloud environment. Image processing device 203 may include one or more processor(s) 308, one or more storage device(s) 304, and one or more memory device(s) 306. Processor(s) 308, storage device(s) 304, and memory device(s) 306 may be configured in a centralized or a distributed manner. Image processing device 203 may also include an image database (optionally stored in storage device 304 or in a remote storage), an input/output device (not shown, but which may include a touch screen, keyboard, mouse, speakers/microphone, or the like), a network interface such as communication interface 302, a display (not shown, but which may be a cathode ray tube (CRT) or liquid crystal display (LCD) or the like), and other accessories or peripheral devices. The various elements of image processing device 203 may be connected by a bus 310, which may be a physical and/or logical bus in a computing device or among computing devices.

Processor 308 may be a processing device that includes one or more general processing devices, such as a microprocessor, a central processing unit (CPU), a graphics processing unit (GPU), and the like. More specifically, processor 308 may be a complex instruction set computing (CISC) microprocessor, a reduced instruction set computing (RISC) microprocessor, a very long instruction word (VLIW) microprocessor, a processor running other instruction sets, or a processor that runs a combination of instruction sets. Processor 308 may also be one or more dedicated processing devices such as application specific integrated circuits (ASICs), field programmable gate arrays (FPGAs), digital signal processors (DSPs), system-on-chip (SoCs), and the like.

Processor 308 may be communicatively coupled to storage device 304/memory device 306 and configured to execute computer-executable instructions stored therein. For example, as illustrated in FIG. 3, bus 310 may be used, although a logical or physical star or ring topology would be examples of other acceptable communication topologies. Storage device 304/memory device 306 may include a read only memory (ROM), a flash memory, random access memory (RAM), a static memory, a volatile or non-volatile, magnetic, semiconductor, tape, optical, removable, non-removable, or other type of storage device or tangible (e.g., non-transitory) computer readable medium. In some embodiments, storage device 304 may store computer-executable instructions of one or more processing programs used for the processing and data generated when a computer program is executed. The data may be read from storage device 304 one by one or simultaneously and stored in memory device 306. Processor 308 may execute the processing program to implement each step of the methods described below. Processor 308 may also send/receive medical data to/from storage device 304/memory device 306 via bus 310.

Image processing device 203 may also include one or more digital and/or analog communication (input/output) devices, not illustrated in FIG. 3. For example, the input/output device may include a keyboard and a mouse or trackball that allow a user to provide input. Image processing device 203 may further include a network interface, illustrated as communication interface 302, such as a network adapter, a cable connector, a serial connector, a USB connector, a parallel connector, a high-speed data transmission adapter such as optical fiber, USB 3.0, lightning, a wireless network adapter such as a WiFi adapter, or a telecommunication (3G, 4G/LTE, etc.) adapter and the like. Image processing device 203 may be connected to a network through the network interface. Image processing device 203 may further include a display, as mentioned above. In some embodiments, the display may be any display device suitable for displaying a medical image and its diagnostic results. For example, the image display may be an LCD, a CRT, or an LED display.

Image processing device 203 may be connected, wired or wirelessly, to image acquisition device 205A, . . . , 205N as discussed above with reference to FIG. 2. Other implementations are also possible.

Figure 4:
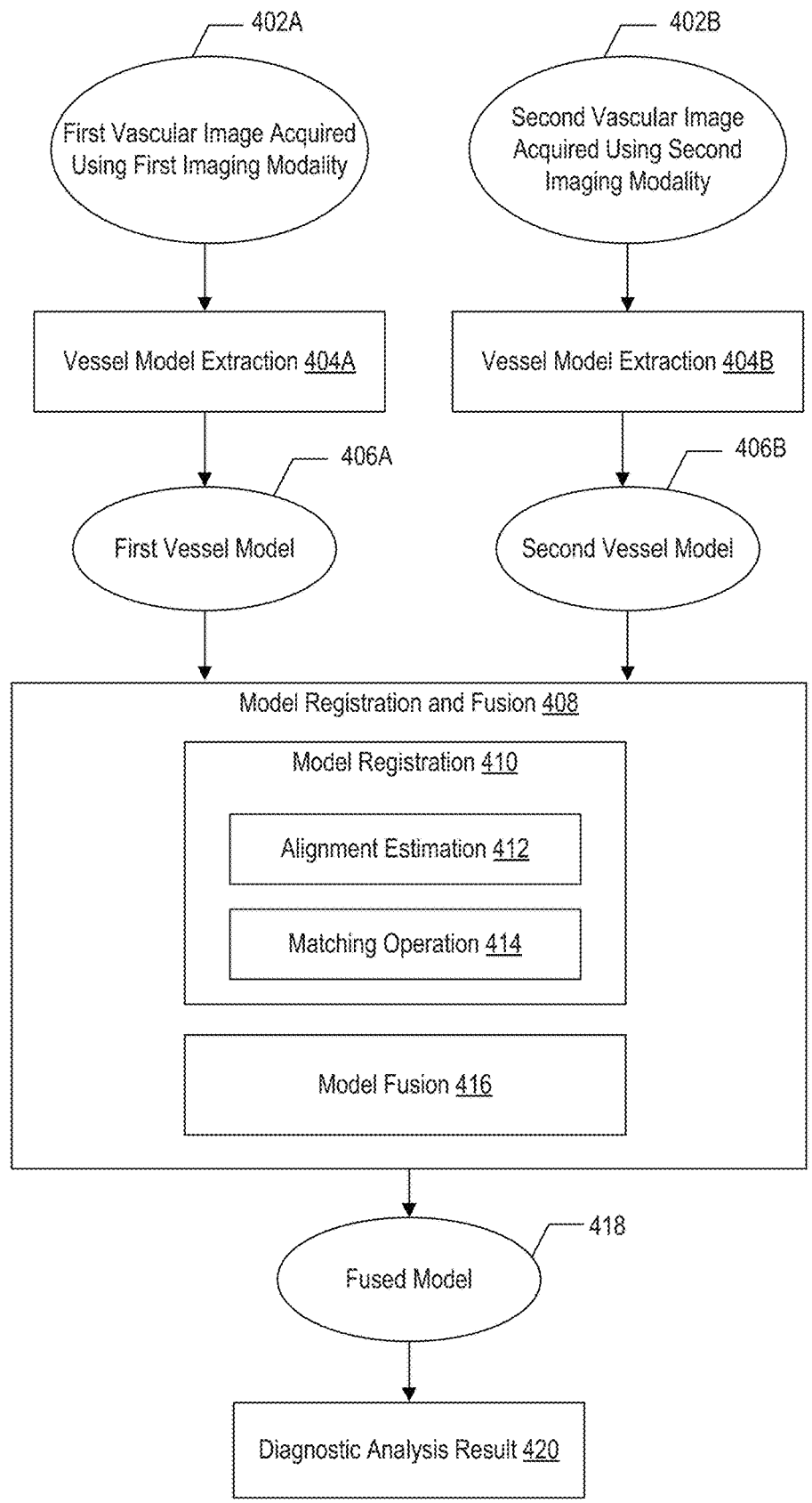
FIG. 4 illustrates a schematic diagram of an exemplary framework of multi-modality joint analysis of vascular images, according to certain embodiments of the disclosure.

FIG. 4 illustrates a schematic diagram of an exemplary framework of multi-modality joint analysis of vascular images, according to certain embodiments of the disclosure, Specifically, image processing device 203 may perform vessel extraction for each individual imaging modality to generate a respective vessel model, so that a plurality of vessel models can be generated for a plurality of imaging modalities. Then, image processing device 203 may perform model registration and fusion for the plurality of vessel models to generate a fused model. For example, image processing device 203 may register the plurality of vessel models from different imaging modalities into the same physical space, and then fuse the plurality of vessels model to generate a fused model for further quantification analysis, functional evaluation (e.g., FFR, iFR, etc.), or visualization.

It is contemplated that the plurality of imaging modalities may include two or more imaging modalities, and not all the imaging modalities disclosed herein have to be present for the multi-modality joint analysis disclosed herein. The multi-modality joint analysis can be carried out among different imaging modalities belonging to the same modality group. For example, the multi-modality joint analysis can be carried out based on MRA and CTA, which are both 3D angiography. Alternatively, the multi-modality joint analysis can be carried out among imaging modalities belonging to different modality groups. For example, the multi-modality joint analysis can be carried out based on CTA (which belongs to 3D angiography) and OCT (which belongs to intravascular imaging).

An exemplary process of multi-modality joint analysis of vascular images is provided herein with reference to FIG. 4. Initially, imaging processing device 203 may receive one or more first vascular images 402A acquired using a first imaging modality and one or more second vascular images 402B acquired using a second imaging modality. Each of the first and second imaging modalities can be 3D angiography (such as CTA or MRA), intravascular imaging (such as OCT or IVUS), or invasive XA. Each vascular image 402A or 402B includes a vessel of interest.

Next, imaging processing device 203 may extract a first vessel model 406A and a second vessel model 406B for the vessel of interest from the one or more first vascular images 402A and the one or more second vascular images 402B, respectively. For example, imaging processing device 203 may perform a vessel model extraction operation 404A on the one or more first vascular images 402A to generate first vessel model 406A. First vessel model 406A is associated with the first imaging modality, First vessel model 406A may include a vessel structure including at least one of a centerline, a radius, or a segmentation mask, etc., of the vessel of interest for the first imaging modality. Consistent with the present disclosure, a "centerline" may be a skeleton line of the vessel of interest, and may generally track the vessel of interest, including one or more "trunks" and/or one or more "branches" of the vessel of interest.

In another example, imaging processing device 203 may perform a vessel model extraction operation 404B on the one or more second vascular images 402B to generate second vessel model 406B. Second vessel model 406B is associated with the second imaging modality. Second vessel model 406B may include a vessel structure including at least one of a centerline, a radius, or a segmentation mask, etc., of the vessel of interest for the second imaging modality. Vessel model extraction operation 404A or 404B is described below in more detail with reference to FIG. 5.

Further, image processing device 203 may fuse first and second vessel models 406A and 406B to generate a fused model 418 for the vessel of interest. For example, image processing device 203 may determine a correspondence between first and second vessel models 406A, 406B, and fuse first and second vessel models 406A, 406B based on the correspondence of first and second vessel models 406A, 406B. In a further example, first vessel model 406A is a 2D model and second vessel model 406B is a 3D model. Image processing device 203 may determine a correspondence between the 2D model and the 3D model, and fuse the 2D model and the 3D model based on the correspondence of the 2D model and the 3D model. In another further example, first vessel model 406A is a first 3D model and second vessel model 406B is a second 3D model. Image processing device 203 may determine a correspondence between the first D model and the second 3D model, and fuse the first and second 3D models based on the correspondence of the first and second 3D models.

In some embodiments, image processing device 203 may perform a model registration and fusion operation 408 (including a model registration operation 410 and a model fusion operation 416) on first and second vessel models 406A and 406B to generate fused model 418. Fused model 418 may be a registered multi-modality joint model for the vessel of interest and generated by the fusion of first and second vessel models 406A and 406B. Image processing device 203 may determine the correspondence between first and second vessel models 406A, 406B by performing model registration operation 410.

To perform in model registration operation 410 to determine the correspondence between first and second vessel models 406A, 406B), image processing device 203 may register first and second vessel models 406A and 406B into a common physical space. For example, image processing device 203 may perform an alignment estimation operation 412 to estimate an alignment relationship between first and second vessel models 406A and 406B, so that first and second vessel models 406A and 406B are aligned with one another based on the alignment relationship. Alternatively or additionally, image processing device 203 may perform a matching operation 414 on first and second vessel models 406A and 406B so that first and second vessel models 406A and 406B are matched with one another.

For example, to perform model registration operation 410 (to determine the correspondence between first and second vessel models 406A, 406B), image processing device 203 may perform a projection pose estimation to estimate a geometric relationship between first and second vessel models 406A, 406B, so that first and second vessel models 406A, 406B are aligned with one another based on the geometric relationship. Image processing device 230 may perform a point matching operation to match a first reference pattern of the vessel of interest in first vessel model 406A with a second reference pattern of the vessel of interest in second vessel model 406B.

In another example, to perform model registration operation 410 (e.g., to determine the correspondence between first and second vessel models 406A, 406B), image processing device 203 may perform a longitudinal shift estimation to estimate a longitudinal relationship between first and second vessel models 406A, 406B, so that a longitudinal location of first vessel model 406A is aligned with a longitudinal location of second vessel model 406B based on the longitudinal relationship. Image processing device 103 may perform a cross-sectional matching operation on first and second vessel models 406A, 406B.

Then, image processing device 203 may perform model fusion operation 416 to fuse first and second vessel models 406A and 406B to generate fused model 418 based on the registration of first and second vessel models 406A and 406B. Model registration and fusion operation 408 (including alignment estimation operation 412, matching operation 414, and model fusion operation 416) are described below in more detail with reference to FIGS. 6-7.

Image processing device 203 may provide a diagnostic analysis result 420 based on fused model 418 of the vessel of interest. For example, image processing device 203 may perform functional analysis based on fused model 418 so that an FFR or iFR analysis result of the vessel of interest may be generated. In some embodiments, first and second vessel models 406A and 406B may include a 2D model and a 3D model, respectively, and image processing device 203 may provide an improved vessel reconstruction with a 3D shape of the vessel of interest from the 3D model and vessel and lesion characteristics from the 2D model. For example, if fused model 418 is combined from a first vessel model associated with CTA and a second vessel model associated with OCT, image processing device 203 may provide an improved vessel reconstruction with a 3D shape of the vessel of interest acquired using CTA and vessel and lesion characteristics acquired using OCT. In some embodiments, image processing device 203 may provide immersive visualization of the vessel of interest in augmented or virtual reality to visualize a structure of the vessel of interest and/or lesions of the vessel of interest. For example, based on fused model 418 which combines imaging details of CTA and XA, immersive visualization of the vessel of interest in augmented and/or virtual reality can be provided to visualize an artery structure and disease comprehensively. Other exemplary diagnosis analysis results are also possible.

Figure 5:
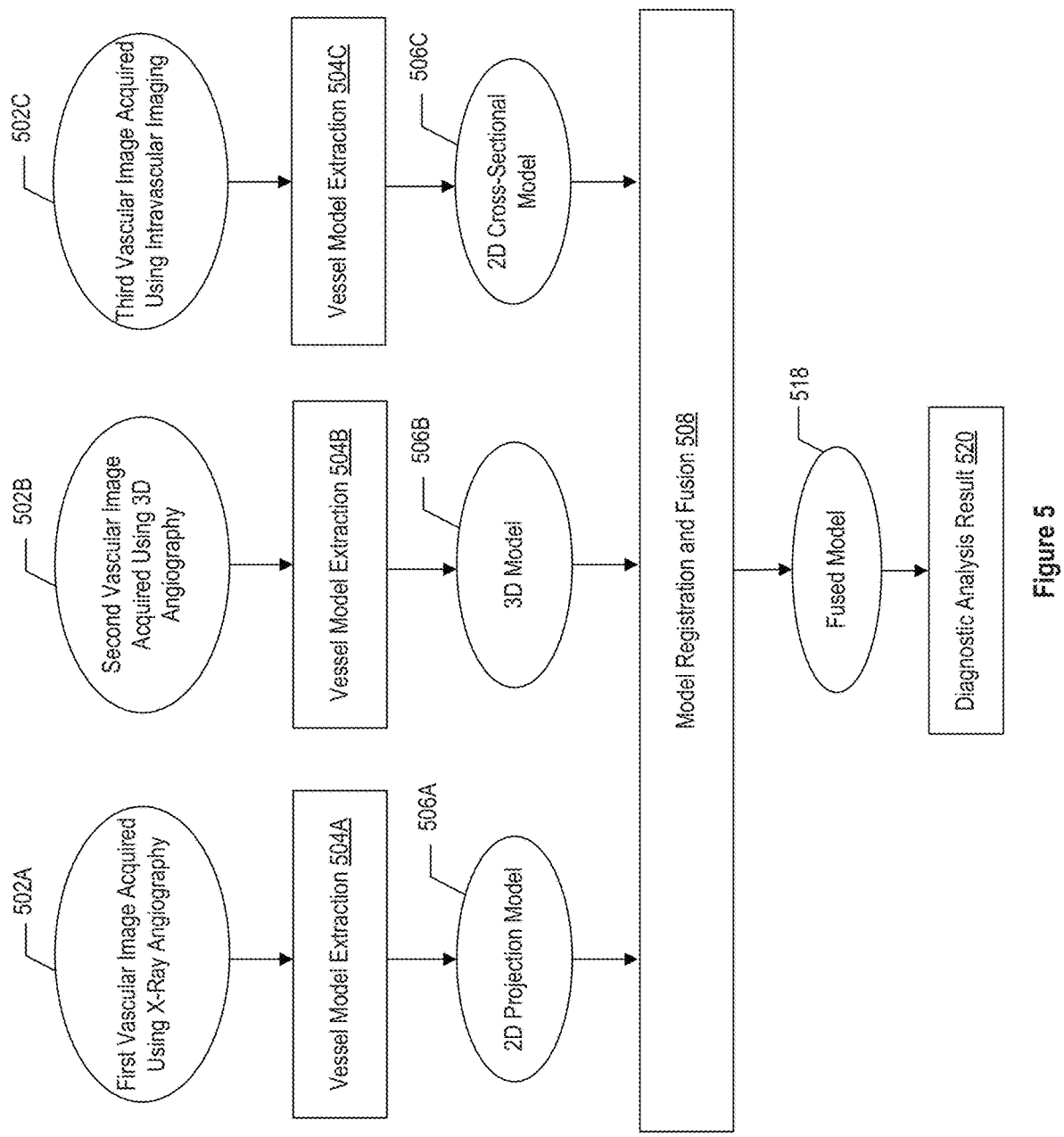
FIG. 5 illustrates a schematic diagram of another exemplary framework of multi-modality joint analysis of vascular images, according to certain embodiments of the disclosure.

FIG. 5 illustrates a schematic diagram of another exemplary framework of multi-modality joint analysis of vascular images, according to certain embodiments of the disclosure. FIG. 5 can be viewed as an exemplary implementation of FIG. 4. Initially, imaging processing device 203 may receive one or more first vascular images 502A acquired using a first imaging modality (e.g., XA), one or more second vascular images 502B acquired using a second imaging modality (e.g., 3D angiography), and one or more third vascular images 502C acquired using a third imaging modality (e.g., intravascular imaging). Each vascular image (e.g., 502A, 502B, or 502C) includes a vessel of interest.

Next, imaging processing device 203 may extract a first vessel model (e.g., a 2D projection model 506A), a second vessel model (e.g., a 3D model 506B), and a third vessel model (e.g., a 2D cross-sectional model 506C) for the vessel of interest from the one or more first vascular images 502A, the one or more second vascular images 502B, and the one or more third vascular images 502C, respectively.

In some embodiments, imaging processing device 203 may perform a vessel model extraction operation 504A on the one or more first vascular images 502A to generate 2D projection model 506A. Vessel model extraction operation 504A may include vessel centerline extraction and/or vessel segmentation performed on the one or more first vascular images 502A. 2D projection model 506A may include a 2D vessel structure including at least one of a centerline, a radius, or a segmentation mask, etc., of the vessel of interest acquired using XA.

For example, the one or more first vascular images 502A (e.g., XA images) may include a series of 2D frames that record several seconds of a video showing the vessel of interest filled with contrast material and projected from a certain angle. One or more frames (e.g., a key frame or all the frames) from the series of 2D frames can be selected for vessel structure extraction to derive at least one of a centerline, a diameter, or a segmentation mask of the vessel of interest, etc. The extracted vessel structure can be an entire vessel tree including all the branches shown in the one or more frames, a single branch of the vessel tree, or a subset of the branches of the vessel tree.

In some embodiments, imaging processing device 203 may perform a vessel model extraction operation 504B on the one or more second vascular images 502B to generate 3D model 506B. Vessel model extraction operation 504B may include vessel centerline extraction and/or vessel segmentation performed on the one or more second vascular images 502B. 3D model 506B may include a 3D vessel structure including at least one of a centerline, a radius, or a segmentation mask of the vessel of interest acquired using 3D angiography.

For example, 3D angiography generates a 3D image at each acquisition time or a 4D (3D+time) image sequence over a period of time (e.g., the 4D image sequence may include a sequence of 3D images acquired by 3D angiography over the period of time). Thus, the one or more second vascular images 502B may include a series of 3D images acquired by 3D angiography. A 3D vessel structure can be extracted from the series of 3D images in the for of a centerline, a diameter, a centerline plus a diameter, a segmentation mask, 2D cross-sectional images, 3D image patches, or volumetric images, etc.

In some embodiments, imaging processing device 203 may perform a vessel model extraction operation 504C on the one or more third vascular images 502C to generate 2D cross-sectional model 506C. Vessel model extraction operation 504C may include vessel lumen segmentation performed on the one or more third vascular images 502C. 2D cross-sectional model 506C may include a sequence of 2D cross-sectional vessel structures. Each 2D cross-sectional vessel structure including at least one of a radius or a segmentation mask of the vessel of interest acquired using intravascular imaging. For example, intravascular imaging can be used to generates a series of 2D cross-sectional image frames of a vessel (e.g., which is typically a single branch of the vessel as the imaging "camera/sensor" traverses inside the vessel). The extracted vessel structure can be in the form of a diameter or a segmentation mask at each cross-sectional frame location.

Further, image processing device 203 may fuse 2D projection model 506A, 3D model 506B, and 2D cross-sectional model 506C to generate a fused model 518 for the vessel of interest. For example, image processing device 203 may perform a model registration and fusion operation 508 on 2D projection model 506A, 3D model 506B, and 2D cross-sectional model 506C. Fused model 518 may be a registered multi-modality joint model of the vessel of interest generated by the fusion of 2D projection model 506A, 3D model 506B, and 2D cross-sectional model 506C. Model registration and fusion operation 508 is also described below in more detail with reference to FIGS. 6-7. Image processing device 203 may then provide a diagnostic analysis result 520 based on fused model 518 of the vessel of interest.

Figure 7:
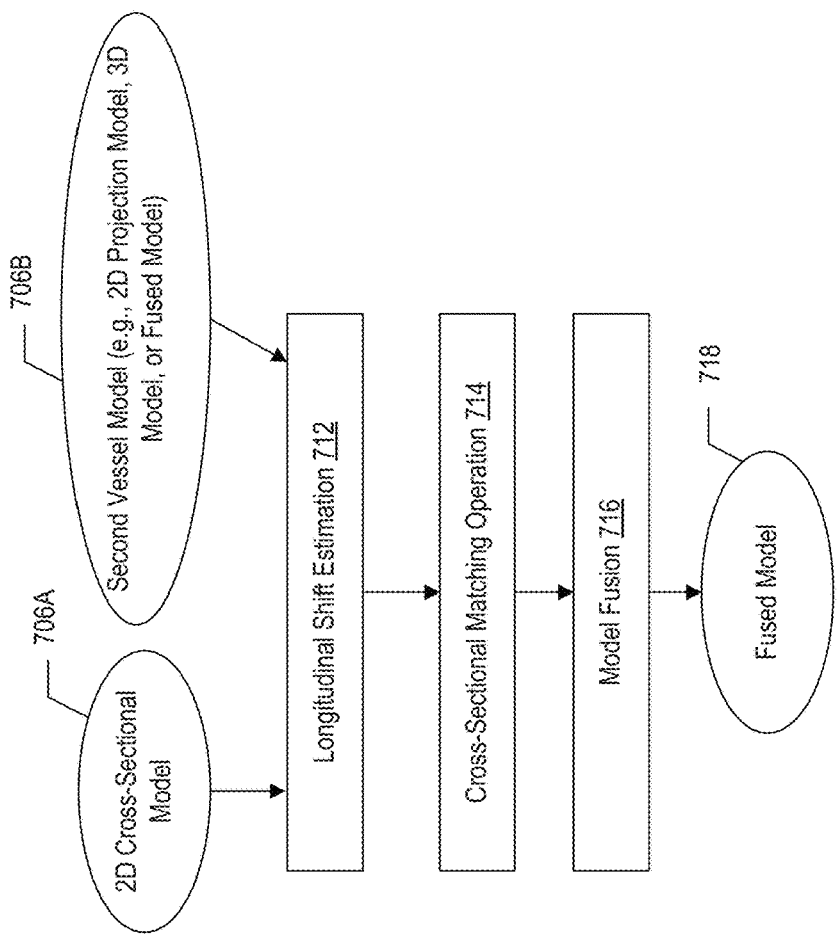
FIG. 7 illustrates a schematic diagram of another exemplary process of model registration and fusion, according to certain embodiments of the disclosure.
Figure 6:
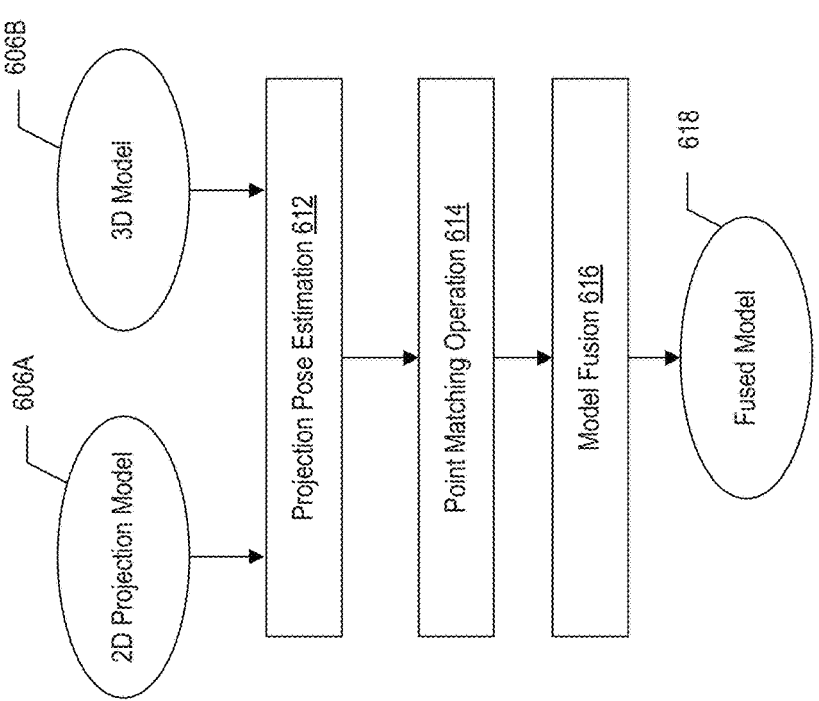
FIG. 6 illustrates a schematic diagram of an exemplary process of model registration and fusion, according to certain embodiments of the disclosure.

Consistent with the present disclosure, registration of different types of imaging modalities can be grouped into one or more categories including, but not limited to, the following: (1) registration of a 2D projection model acquired using XA and a 3D model acquired using 3D angiography, as shown in FIG. 6 below; (2) registration of a 2D cross-sectional model acquired using intravascular imaging and another vessel model acquired using a different imaging modality (e.g., the other vessel model being a 2D projection model acquired using XA, a 3D model acquired using 3D angiography, or a fused model generated from the 2D projection model and the 3D model), as shown in FIG. 7 below; (3) registration of a first 3D model acquired using a first example of 3D angiography (e.g., CTA) and a second 3D model acquired using a second example of 3D angiography (e.g., MRA); or (4) registration of a first 2D cross-sectional model acquired using a first example of intravascular imaging (e.g., OCT) and a second 2D cross-sectional model acquired using a second example of intravascular (e.g., IVUS), etc.

Consistent with the present disclosure, to register first vessel model and a second vessel model, image processing device 203 may perform an alignment estimation to estimate an alignment relationship between the first and second vessel models, as described above with reference to FIG. 4. As a result, the first and second vessel models are aligned with one another based on the alignment relationship. Image processing device 203 may perform a matching operation on the first and second vessel models, so that the first and second vessel models are matched with one another, as described above with reference to FIG. 4. Each of the first and second vessel models can be any type of vessel models disclosed herein, including but not limited to, a 2D projection model, a 3D model, or a 2D cross-sectional model.

For example, the alignment relationship may include a geometric relationship between the first and second vessel models. Image processing device 203 may perform (1) a projection pose estimation to estimate the geometric relationship between the first and second vessel models and (2) a point matching operation to match a first reference pattern of the vessel of interest in the first vessel model with a second reference pattern of the vessel of interest in the second vessel model, as described below in more detail with reference to FIG. 6.

In another example, the alignment relationship may a longitudinal relationship between the first and second vessel models. Image processing device 203 may perform a longitudinal shift estimation to estimate the longitudinal relationship between the first and second vessel models, so that a longitudinal location of the first vessel model is aligned with a longitudinal location of the second vessel model based on the longitudinal relationship. Image processing device 203 may also perform a cross-sectional matching operation on the first and second vessel models, as described below in more detail with reference to FIG. 7, FIG. 6 illustrates a schematic diagram of an exemplary process of model registration and fusion between a first vessel model and a second vessel model, according to certain embodiments of the disclosure. FIG. 6 is described below by taking a 2D projection model 606A acquired using XA as an example of the first vessel model and a 3D model 606B acquired using 3D angiography as an example of the second vessel.

3D model 606B may include a whole vessel structure in 3D, whereas 2D projection model 606A may simply be a 2D projection of the vessel at a certain angle. Thus, the registration of 2D projection model 606A and 3D model 606B may include at least one of a projection pose estimation 612 or a point matching operation 614. It is contemplated that projection pose estimation 612 and point matching operation 614 may not be necessarily conducted sequentially in a sequential order and may also be conducted in other ways such as jointly or iteratively.

Specifically, image processing device 203 may perform projection pose estimation 612 to estimate a geometric relationship between 2D projection model 606A and 3D model 606B. The geometric relationship may indicate translation and/or rotation between 3D model 606B and 2D projection model 606A. For example, the geometric relationship may include a translation parameter describing the translation between 2D projection model 606A and 3D model 606B and/or a rotation parameter describing the rotation between 2D projection model 606A and 3D model 606B. Values for the translation and rotation parameters may be recorded in XA imaging meta data. In some applications, these values may not be accurate enough due to patient breathing, heart beating, or table movement, etc. Thus, a projection pose parameter refinement/optimization process may be performed by evaluating and analyzing how well 3D model 606B matches to 2D projection model 606A under the given values of the translation and rotation parameters and adaptively adjusting the values of the translation and rotation parameters based on the evaluation thereof.

Next, image processing device 203 may perform point matching operation 614 to match a first reference pattern of the vessel of interest in 2D projection model 606A with a second reference pattern of the vessel of interest in 3D model 606B. The first reference pattern may include a centerline (and/or, a truck, one or more branches, one or more bifurcations, etc.) of the vessel of interest extracted in 2D projection model 606A. Similarly, the second reference pattern may include a centerline (and/or, a truck, one or more branches, one or more bifurcations, etc.) of the vessel of interest extracted in 3D model 606B.

For example, point matching operation 614 may be used to further match a 3D vessel centerline from 3D model 606B to a 2D vessel centerline from 2D projection model 606A (e.g., a point-to-point matching between the 3D vessel centerline and the 2D vessel centerline may be performed). Point matching operation 614 may handle non-rigid deformation between 3D model 606B and 2D projection model 606A, which is not handled by projection pose estimation 612. This non-rigid deformation may be inherent. For example, the heart in vascular images acquired using 3D angiography and the heart in vascular images acquired using 2D XA may be in different phases of a heart beating cycle, which may lead to non-rigid deformation of the coronary artery shape. Point matching operation 614 can be performed to reduce or eliminate the non-rigid deformation on the whole vessel tree or only on a vessel branch.

In some embodiments, image processing device 203 may utilize various information to perform the point-to-point matching in point matching operation 614, including but not limited to, an initial registration (e.g., projection pose estimation) of 3D model 606B and 2D projection model 606A, vessel radius information extracted from each imaging modality, and landmark points such as bifurcation points detected in each imaging modality, etc. A further example of point matching operation 614 is described below in more detail with reference to FIGS. 8A-8B, 9A-9C, and 10.

In some embodiments, additional landmarks such as vessel bifurcations may be introduced and used to further improve the registration result of 3D model 606B and 2D projection model 606A in both projection pose estimation 612 and point matching operation 614.

Further, after 2D projection model 606A and 3D model 606B are registered through projection pose estimation 612 and/or point matching operation 614, image processing device 203 may perform a model fusion operation 616 on 3D model 606B and 2D projection model 606A to generate a fused model 618. For example, image processing device 203 may apply a fusing strategy to fuse 3D model 606B and 2D projection model 606A to generate fused model 618. Image processing device 203 may determine the fusing strategy based on specific application scenarios.

In an exemplary scenario, a lumen diameter extracted from XA. (which is more reliable than that extracted from 3D angiography) can be used to modify a 3D vessel segmentation mask or mesh model from the 3D CTA, so that the problem of ambiguous lumen boundary around calcium in 3D CTA can be alleviated. In another exemplary scenario, the recovering of a 3D model from a single 2D projection image acquired using XA is generally impossible due to the lack of 3D depth information. However, a 3D vessel shape extracted from the 3D angiography can be helpful for recreating the 3D vessel model from the single 2D projection image from XA. The fused model generated thereof may be a 3D vessel model that incorporates the 3D vessel shape extracted from the 3D angiography and a 2D projection model extracted from the single 2D projection image.

FIG. 7 illustrates a schematic diagram of another exemplary process of model registration and fusion between a first vessel model and a second vessel model, according to certain embodiments of the disclosure. By way of examples, the first vessel model is a 2D cross-sectional model 706A acquired using intravascular imaging, and the second vessel model 706B can be a 2D projection model acquired using XA, a 3D model acquired using 3D angiography, or a fused model generated based on the 2D projection model and the 3D model.

A series of 2D cross-sectional image frames may be acquired with intravascular imaging when a catheter is traversing inside a segment of a vessel of interest. Image processing device 203 may extract 2D cross-sectional model 706A from the series of 2D cross-sectional image frames. The registration of 2D cross-sectional model 706A and second vessel model 706B may include assigning a longitudinal location to each 2D cross-sectional image frame and determining an optimal rotation and translation within individual 2D cross-sectional image frames to match second vessel model 706B. Thus, the registration of 2D cross-sectional model 706A and second vessel model 706B may include a longitudinal shift estimation 712 and/or a cross-sectional matching operation 714. It is contemplated that longitudinal shift estimation 712 and cross-sectional matching operation 714 may not be necessarily conducted sequentially in a sequential order, and may also be conducted in other ways such as jointly or iteratively.

Specifically, image processing device 203 may perform longitudinal shift estimation 712 to estimate a longitudinal relationship between 2D cross-sectional model 706A and second vessel model 706B, so that a longitudinal location of 2D cross-sectional model 706A is aligned with a longitudinal location of second vessel model 706B based on the longitudinal relationship. In some embodiments, image processing device 203 may perform longitudinal shift estimation 712 by comparing and matching various vessel information such as vessel bifurcations, lesion locations, vessel diameters, vessel segmentation mask overlaps, etc., between 2D cross-sectional model 706A and second vessel model 706B.

For example, 2D cross-sectional model 706A may include a particular bifurcation (or a lesion location, etc.) extracted from a 2D cross-sectional image frame. Second vessel model 706B may also include the same vessel bifurcation (or the same lesion location, etc.) extracted from a 2D XA image or a 3D CTA image. By comparing 2D cross-sectional model 706A with second vessel model 706B, image processing device 203 may determine a longitudinal location of the 2D cross-sectional image frame to be the same as a longitudinal location of the same vessel bifurcation (or, the same lesion location, etc.) in the 2D XA image or the 3D CTA image.

Alternatively or additionally, image processing device 203 may perform cross-sectional matching operation 714 to match 2D cross-sectional model 706A with second vessel model 706B. In some embodiments, image processing device 203 may perform in cross-sectional matching operation 714 by comparing and matching various vessel information such as a vessel bifurcation direction, a lesion shape, a cross-sectional segmentation mask shape, a diameter profile, etc.

For example, 2D cross-sectional model 706A may include a vessel bifurcation direction (or, a lesion shape, etc.) extracted from a 2D cross-sectional image frame. Second vessel model 706B may also include the same vessel bifurcation direction (or, the same lesion shape, etc.) extracted from a 2D XA image or 3D CTA image. By comparing 2D cross-sectional model 706A with second vessel model 706B, image processing device 203 may determine a translation parameter and a rotation parameter within the 2D cross-sectional image frame so that the 2D cross-sectional image frame is matched to the 2D XA image or 3D CTA image. For example, the vessel bifurcation direction (or, the lesion shape, etc.) in the 2D cross-sectional image may match the same vessel bifurcation direction (or, the same lesion shape, etc.) in the 2D XA image or 3D CTA image after the 2D cross-sectional image frame is translated and rotated based on the translation parameter and the rotation parameter, respectively.

In some embodiments, additional landmarks may be introduced and used to further improve the registration result of 2D cross-sectional model 706A and second vessel model 706B in both longitudinal shift estimation 712 and cross-sectional matching operation 714.

Further, after 2D cross-sectional model 706A and second vessel model 706B are registered through longitudinal shift estimation 712 and cross-sectional matching operation 714, image processing device 203 may perform a model fusion operation 716 on 2D cross-sectional model 706A and second vessel model 706B to generate a fused model 718. For example, image processing device 203 may determine a format of fused model 718 based on specific application scenarios. In an exemplary scenario, image processing device 203 may overlay 2D cross-sectional OCT image frames with a 3D model extracted from 3D CTA to generate a fused model, which enables a virtual 3D endoscopy-like "walk-through" of the vessel segment of interest. Based on the fused model, a user can easily see the details of lesion presented by the OCT image frames, as well as an overall 3D shape of the whole vessel tree and bifurcation patterns presented by CTA images.

Two examples of multi-modality joint analysis of vascular images are provided herein. A first example of multi-modality joint analysis involves XA and CTA. One or more 2D XA images may be captured by an X-ray detector through XA. One or more 3D CTA images may also be obtained through CTA. The one or more XA images and the one or more CTA images can be rigidly registered by estimating their relative pose (e.g., by projection pose estimation). The pose can be parameterized by translation (e.g., 3 translation parameters) and rotation 3 rotation parameters). In an exemplary implementation, image processing device 203 may perform vessel segmentation on the one or more CTA images and further extract a 3D model (e.g., a vessel structure including 3D centerlines of a vessel of interest, which are also referred to as "CTA centerlines"), as shown in FIGS. 8A-8B. FIG. 8A illustrates exemplary CTA vessel segmentation of a vessel 802 of interest. FIG. 8B illustrates 3D CTA centerline extraction of vessel 802.

Figure 9C:
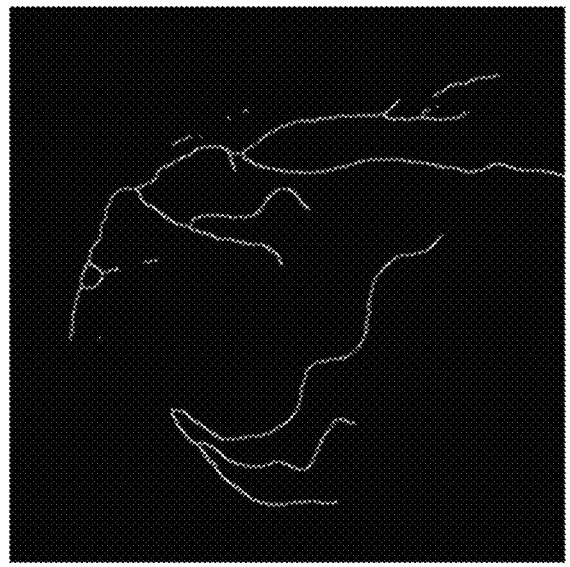
FIGS. 9A-9C are graphical representations illustrating exemplary XA vessel segmentation and 2D centerline extraction, according to certain embodiments of the disclosure.
Figure 9B:
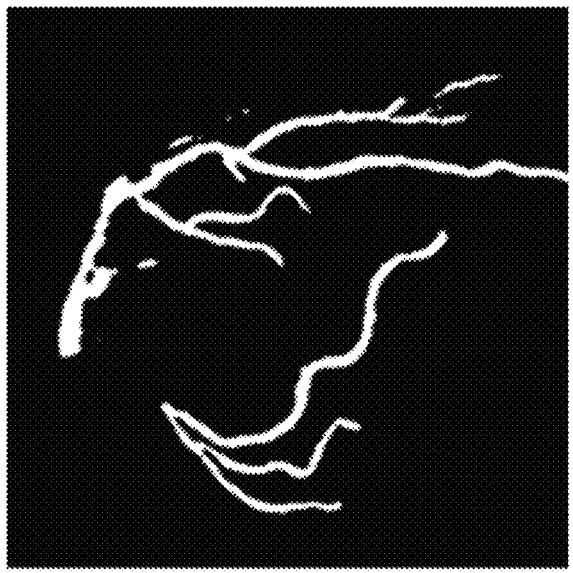
Figure 9A:
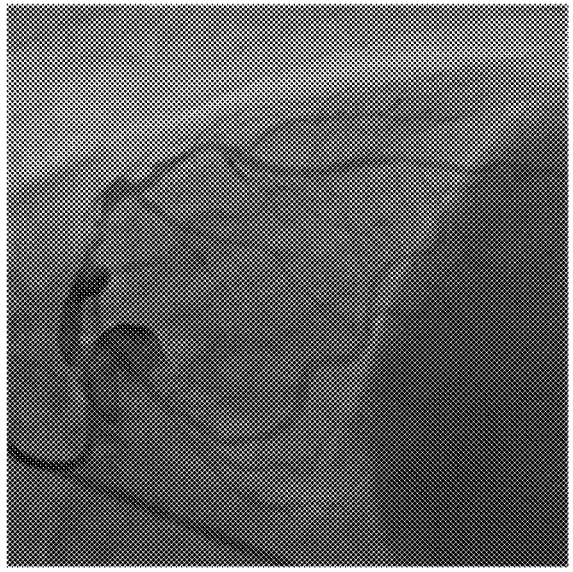

Similarly, image processing device 203 may perform vessel segmentation on the one or more XA images and further extract a 2D projection model (e.g., a vessel structure including 2D centerlines of the vessel of interest, which are also referred to as "XA centerlines"), as shown in FIGS. 9A-9C. FIG. 9A illustrates an exemplary 2D XA image of the vessel of interest. FIG. 9B illustrates an exemplary segmentation mask for the vessel of interest. 9C illustrates 2D XA centerline extraction of the vessel of interest.

Then, the registration of the 2D projection model and the 3D model can be performed by conducting a projection pose estimation. The projection pose estimation includes determining 6 optimized pose parameters (e.g., 3 translation parameters and 3 rotation parameters) that optimizes the matching between the extracted vessel structure in the 2D projection model and the extracted vessel structure in the 3D model. Different strategies can be performed to determine the optimized pose parameters.

An exemplary way is to project the CTA vessel masks into XA views and determine corresponding mask overlap scores. A mask overlap score can be determined using different measures, such as Intersection Over Union (IOU, also known as the Jaccard Index), a dice score, etc. Another exemplary way is to project the CTA centerlines into XA views and to determine a centerline closeness score between the CTA centerlines extracted from the CTA images and the XA centerlines extracted from the XA images. To measure the centerline closeness score, Chamfer distance can be used. In yet another exemplary way, anatomical landmarks that can be identified in both the CTA images and the XA images can be used to determine a matching score. In some embodiments, the optimized pose parameters may be pose parameters that achieve at least one of a highest mask overlap score, a highest centerline closeness score, or a highest matching score. The optimization of the pose parameters can also be performed with different strategies, including coarse-to-fine searching, grid searching, or gradient descent optimization, etc.

Figure 10:
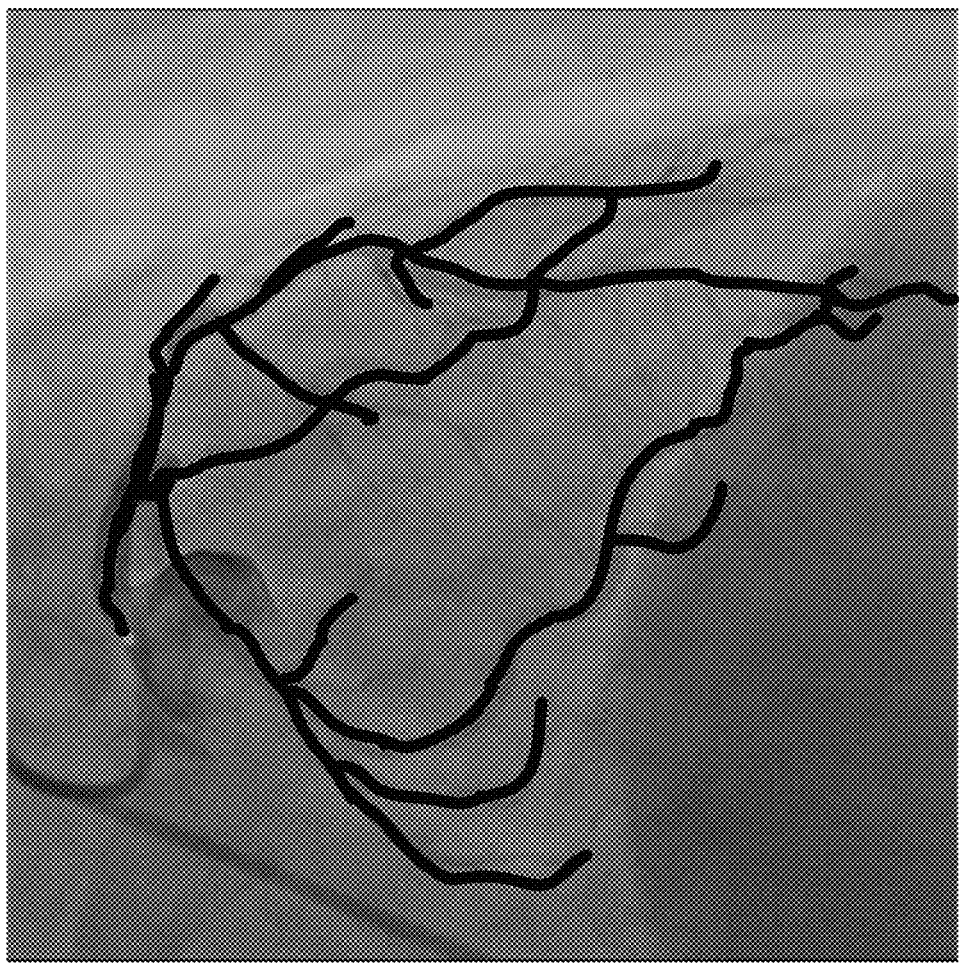
FIG. 10 is a graphical representation illustrating an exemplary registration result of a 2D projection model acquired using XA and a 3D model acquired using CTA, according to certain embodiments of the disclosure.

For example, FIG. 10 is a graphical representation illustrating an exemplary registration result of a 2D projection model acquired using XA and a 3D model acquired using CTA, according to certain embodiments of the disclosure. The background image in FIG. 10 is a 2D XA image. The bold lines in FIG. 10 illustrate the CTA centerlines projected into the 2D XA image according to the optimized pose parameters obtained through the registration of the 2D projection model and the 3D model.

After performing the projection pose estimation, a point matching operation may be performed. For example, image processing device 203 may perform a matching between points on the XA centerlines and points on the CTA centerlines (e.g., a point-to-point matching between the XA centerlines and the CTA centerlines). This matching can be performed on the whole vessel tree, or only on a vessel branch. Additional information can also be utilized to perform the point-to-point matching, including but not limited to, a result of the projection pose estimation, vessel radius information extracted from each imaging modality, and landmark points such as bifurcation points detected in each imaging modality, etc. After the point-to-point matching, centerlines and radius information from the different imaging modalities can be merged to construct a fused model.

Figure 11B:
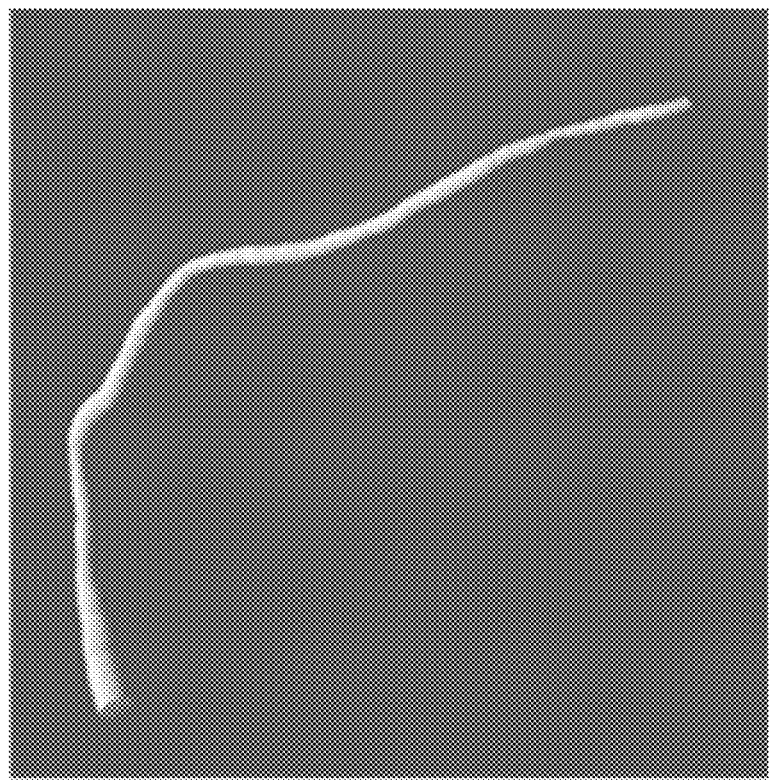
FIGS. 11A-11B are graphical representations illustrating an exemplary fused model for a Left Anterior Descending (LAD) artery branch generated from a 2D projection model acquired using XA and a 3D model acquired using CTA, according to certain embodiments of the disclosure.
Figure 11A:
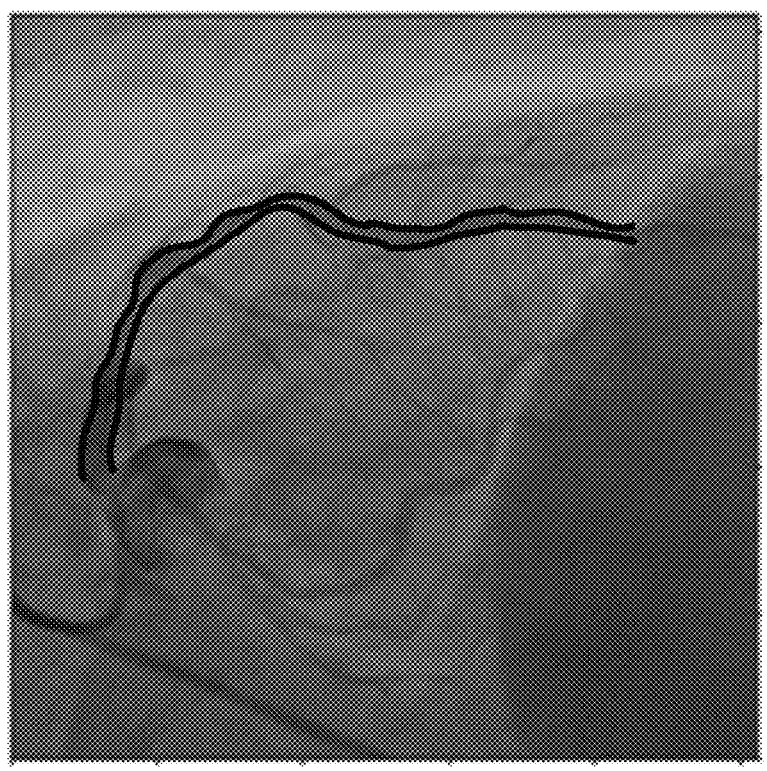

For example, FIGS. 11A-11B are graphical representations illustrating an exemplary fused model for the LAD artery branch generated from a 2D projection model acquired using XA and a 3D model acquired using CTA, according to certain embodiments of the disclosure. FIG. 11A illustrates the 2D projection model (e.g., the LAD vessel structure extracted from XA), with the LAD artery depicted using bold lines, FIG. 11B illustrates the fused model (e.g., a joint reconstruction of the LAD artery) generated based on the 2D projection model (e.g., the LAD vessel structure extracted from XA) and the 3D model (e.g., the LAD vessel structure extracted from CTA). In some implementations, image processing device 203 can utilize the CTA centerline information (extracted from CTA images) and the radius information of the LAD artery (extracted from XA images) to perform the joint reconstruction of the LAD artery.

A second example of multi-modality joint analysis of vascular images involves: (1) OCT; and (2) XA-CTA. XA-CTA herein may refer to XA, CTA, or a combination of XA and CTA. Initially, image processing device 203 may perform OCT lumen segmentation on a video including a plurality of 2D cross-sectional image frames acquired using OCT (e.g., OCT images) and obtain a first vessel model (e.g., a 2D cross-sectional OCT model) thereof. The OCT lumen segmentation can be performed frame by frame (or as a whole sequence of image frames) with typical image segmentation methods, such as U-Net style neural network models (as shown in FIG. 12).

Figure 12:
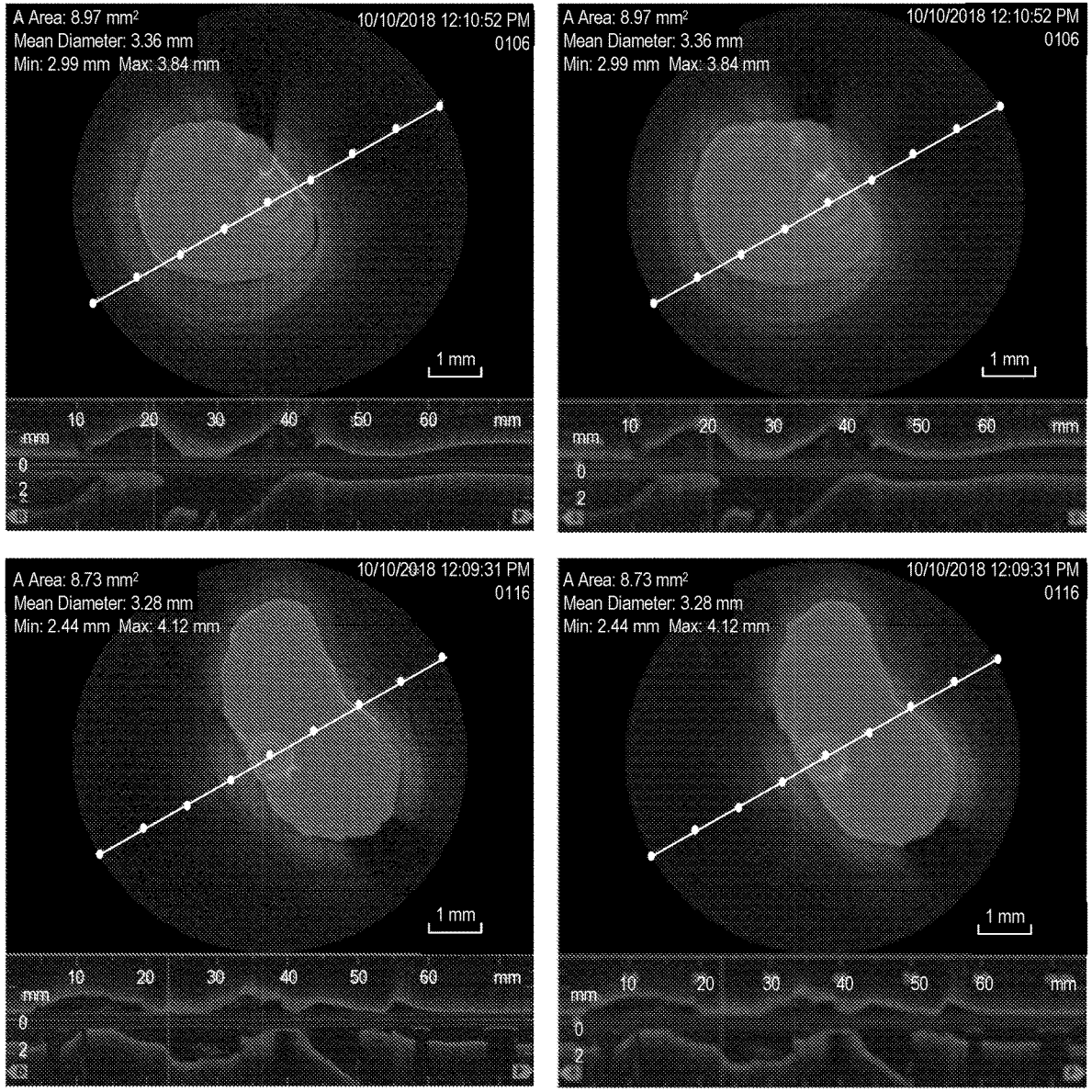
FIG. 12 is a graphical representation illustrating exemplary OCT lumen segmentation, according to certain embodiments of the disclosure.

For example, FIG. 12 is a graphical representation illustrating exemplary OCT lumen segmentation, according to certain embodiments of the disclosure. The left column of FIG. 12 shows ground-truth lumen masks, while the right column shows lumen segmentation from a trained U-Net model.

Image processing device 203 may also obtain a second model. For example, the second model can be a 2D projection XA model acquired from an XA image, a 3D CTA model acquired from a CTA image, or a fused model generated based on the 2D projection XA model and the 3D CTA model. The second model is referred to as an XA-CTA model hereinafter. An XA-CTA image herein may refer to the XA image, the CTA image, or a combination of the XA image and the CTA image.

To register the 2D cross-sectional OCT model with the XA-CTA model, all possible vessel branches from root to end in the XA-CTA model (referred to as XA-CTA vessel branches hereinafter) are extracted and straightened, which is similar to how a vessel branch in the 2D cross-sectional OCT model (referred to as OCT vessel branch hereinafter) is represented. Next, the OCT vessel branch and each straightened XA-CTA vessel branch in the XA-CTA model are rendered in a common image spacing resolution. Then, an optimal translation shift is determined to match the OCT vessel branch and each candidate XA-CTA vessel branch by calculating an IOU score between the two segmentation masks of the OCT vessel branch and the candidate XA-CTA vessel branch in the same straightened space.

For example, the IOU score can be determined as an area of the intersection divided by the area of the union. For each translation shift position, OCT image sequence is registered with the XA-CTA image through a rigid transform (translation and rotation) independently for each OCT frame to achieve an optimal IOU score. The IOU score for each translation shift position is the sum of IOU scores under best rigid transform between all the OCT images and the XA-CTA image.

After registration, a fused model (e.g., a joint reconstruction of the vessel of interest) can be built from the 2D projection OCT model and the XA-CTA model. Then, the fused model can be utilized to compute a simulated FFR value to evaluate influence of a lesion of the vessel of interest on a blood flow supply function. With the aid of accurate lumen segmentation, lesion types, and shape characteristics provided by OCT, the simulation of FFR using the XA-CTA and OCT joint analysis can be more accurate than that using XA or CTA alone.

Figure 13:
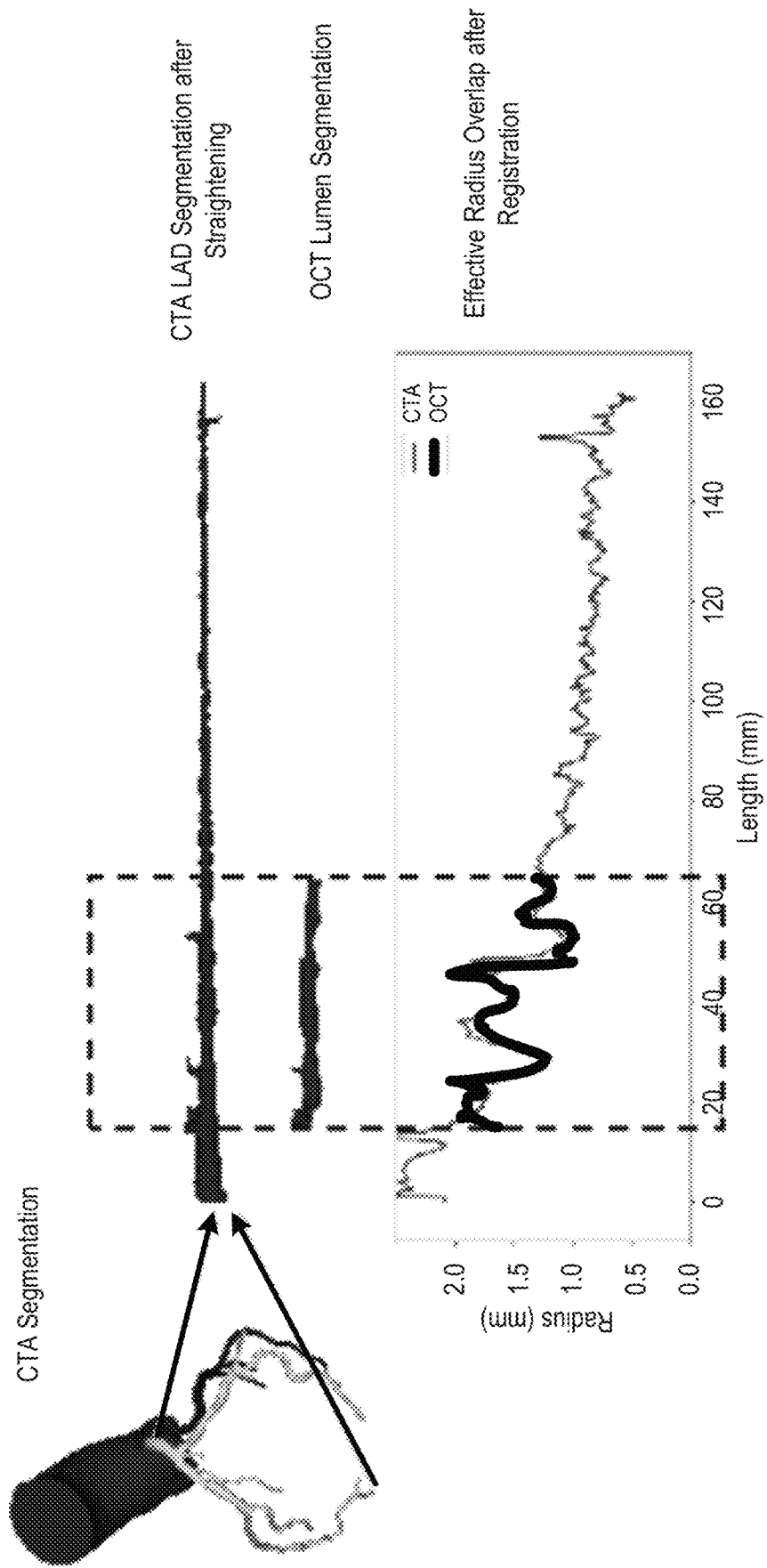
FIG. 13 is a graphical representation illustrating an exemplary registration result of a 2D cross-sectional model acquired using OCT and a 3D model acquired using CTA, according to certain embodiments of the disclosure.

For example, FIG. 13 is a graphical representation illustrating an exemplary registration result of a 2D cross-sectional OCT model and a 3D model acquired using CTA, according to certain embodiments of the disclosure. FIG. 13 shows a CTA segmentation, a CTA LAD segmentation obtained from the CTA segmentation after straightening (which is a 3D CTA model), and an OCT lumen segmentation (which is a 2D cross-sectional OCT model). In FIG. 13, the 3D CTA model is an example of the XA-CTA model (with CTA only). FIG. 13 also shows an effective radius overlap after registration of the 2D cross-sectional OCT model and the 3D CTA model.

Figure 14:
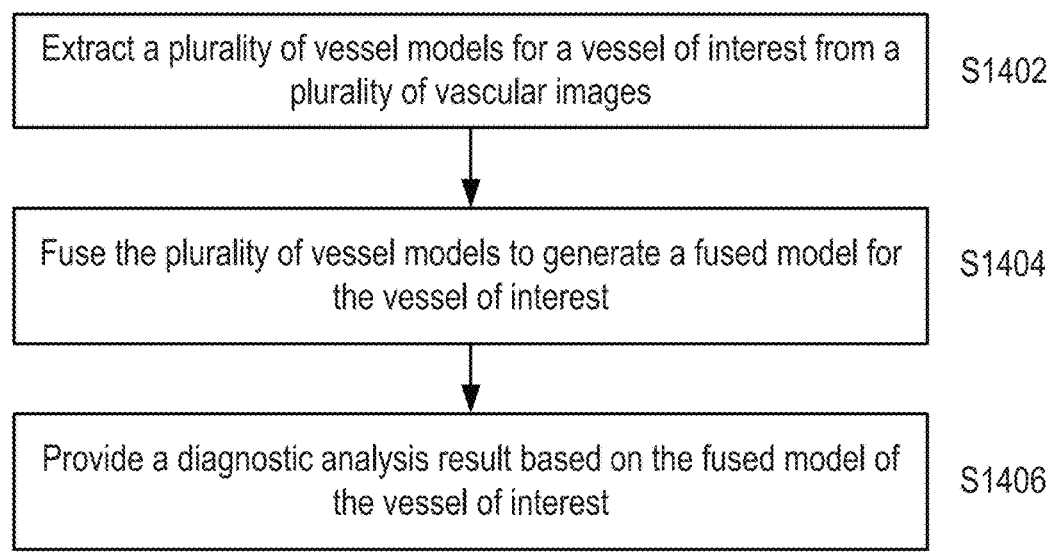
FIG. 14 is a flowchart of an exemplary method for multi-modality joint analysis of vascular images, according to certain embodiments of the disclosure.

FIG. 14 is a flowchart of an exemplary method 1400 for multi-modality joint analysis of vascular images, according to certain embodiments of the disclosure. Method 1400 may be implemented by image processing device 203, and may include steps 1402-1406 as described below. Some of the steps may be optional to perform the disclosure provided herein. Further, some of the steps may be performed simultaneously, or in a different order than shown in FIG. 14.

As shown in FIG. 14, the method may begin, at step S1402, with extracting a plurality of vessel models for a vessel of interest from a plurality of vascular images. The plurality of vascular images are acquired using a plurality of imaging modalities. The plurality of vessel models are associated with the plurality of imaging modalities, respectively.

The method may also include, at step S1404, fusing the plurality of vessel models to generate a fused model for the vessel of interest. For example, image processing device 203 may register the plurality of vessel models into a common physical space, and fuse the plurality of vessel models associated with the plurality of imaging modalities to generate the fused model based on the registration of the plurality of vessel models.

The method may further include, at step S1406, providing a diagnostic analysis result based on the fused model of the vessel of interest. For example, image processing device 203 may perform a functional analysis based on the fused model so that an FFR or iFR analysis result of the vessel of interest may be generated. Other examples of the diagnostic analysis result are also possible.

Figure 15:
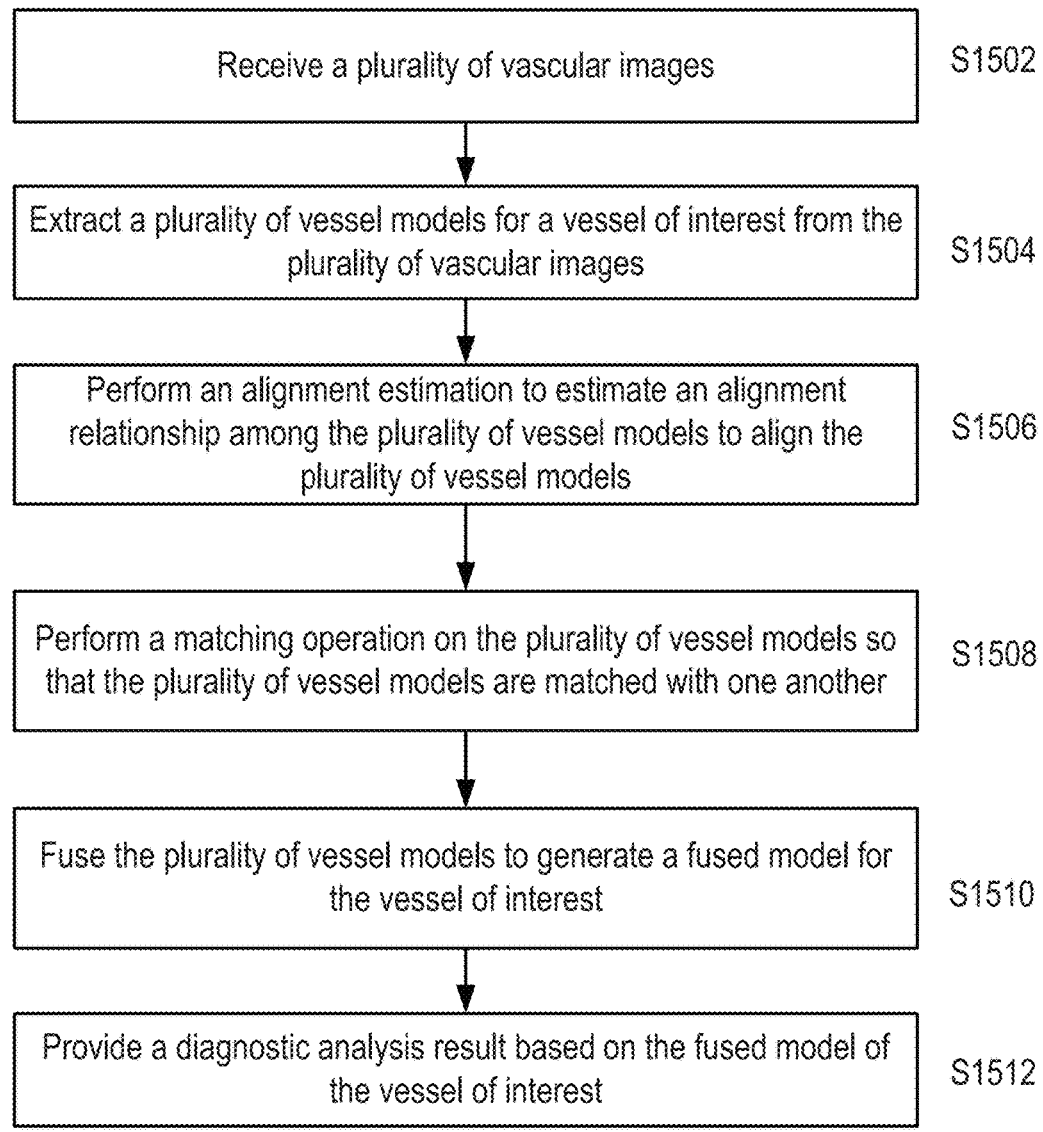
FIG. 15 is a flowchart of another exemplary method for multi-modality joint analysis of vascular images, according to certain embodiments of the disclosure.

FIG. 15 is a flowchart of another exemplary method 1500 for multi-modality joint analysis of vascular images, according to certain embodiments of the disclosure. Method 1500 may be implemented by image processing device 203, and may include steps 1502-1512 as described below. Some of the steps may be optional to perform the disclosure provided herein. Further, some of the steps may be performed simultaneously, or in a different order than shown in FIG. 15.

As shown in FIG. 15, the method may begin, at step S1502, with receiving a plurality of vascular images. For example, communication interface 302 of image processing device 203 may receive a plurality of vascular images acquired using a plurality of imaging modalities.

The method may also include, at step S1504, extracting a plurality of vessel models for a vessel of interest from the plurality of vascular images. The plurality of vessel models are associated with the plurality of imaging modalities, respectively. For example, processor 308 of image processing device 203 may extract a plurality of vessel models for a vessel of interest from the plurality of vascular images.

The method may also include, at step S1506, performing an alignment estimation to estimate an alignment relationship among the plurality of vessel models to align the plurality of vessel models. For example, processor 308 may perform a projection pose estimation to estimate a geometric relationship among the plurality of vessel models, so that the plurality of vessel models are registered into the same physical space through translation and rotation parameters indicated by the geometric relationship. In another example, processor 308 may perform a longitudinal shift estimation to estimate a longitudinal relationship among the plurality of vessel models, so that longitudinal locations of the plurality of vessel models are aligned with one another based on the longitudinal relationship.

The method may also include, at step S1508, performing a matching operation on the plurality of vessel models so that the plurality of vessel models are matched with one another. For example, processor 308 may perform a point matching operation to match reference patterns of the vessel of interest in the plurality of vessel models (e.g., the reference patterns of the vessel of interest n the plurality of vessel models are matched to one another through point-to-point matching). In another example, processor 308 may perform a cross-sectional matching operation on the plurality of vessel models.

The method may further include, at step S1510, fusing the plurality of vessel models to generate a fused model for the vessel of interest.

The method may additionally include, at step S1512, providing a diagnostic analysis result based on the fused model of the vessel of interest.

According to certain embodiments, a non-transitory computer-readable medium may have a computer program stored thereon. The computer program, when executed by at least one processor, may perform a method for multi-modality joint analysis of vascular images. For example, any of the above-described methods may be performed in this way.

While the disclosure uses vascular images as examples that the disclosed systems and methods are applied to analyze, it is contemplated that the disclosed systems and methods can be applied to other types of images beyond vascular images. The images can capture any object, scene, or structures, and an ordinary skill in the art will appreciate that the disclosed systems and methods can be readily adapted to analyze these other images.

In some embodiments, the computer-readable medium may include volatile or non-volatile, magnetic, semiconductor, tape, optical, removable, non-removable, or other types of computer-readable medium or computer-readable storage devices. For example, the computer-readable medium may be the storage device or the memory module having the computer instructions stored thereon, as disclosed. In some embodiments, the computer-readable medium may be a disc or a flash drive having the computer instructions stored thereon.

It will be apparent to those skilled in the art that various modifications and variations can be made to the disclosed system and related methods. Other embodiments will be apparent to those skilled in the art from consideration of the specification and practice of the disclosed system and related methods.

It is intended that the specification and examples be considered as exemplary only, with a true scope being indicated by the following claims and their equivalents.

What is claimed is:

1. A system for multi-modality joint analysis of a plurality of vascular images, comprising:
   a communication interface configured to receive the plurality of vascular images acquired using a plurality of imaging modalities; and
   at least one processor, configured to:
      extract a plurality of vessel models for a vessel of interest from the plurality of vascular images, wherein the plurality of vessel models are associated with the plurality of imaging modalities, respectively, wherein the plurality of vessel models comprise a first vessel model and a second vessel model;
      determine a correspondence among the plurality of vessel models at least by performing a projection pose estimation to estimate one or more pose parameters between the first and second vessel models, wherein the one or more pose parameters indicate an extent of matching between a first vessel structure in the first vessel model and a second vessel structure in the second vessel model;
      fuse the plurality of vessel models associated with the plurality of imaging modalities based on the correspondence to generate a fused model for the vessel of interest; and
      provide a diagnostic analysis result based on the fused model of the vessel of interest.

2. The system of claim 1, wherein:
   the first vessel model is a two-dimensional (2D) model or a first three-dimensional (3D) model and the second vessel model is a second 3D model; and
   to determine the correspondence among the plurality of vessel models, the at least one processor is further configured to:
      determine a correspondence between the 2D model and the second 3D model or a correspondence between the first 3D model and the second 3D model.

3. The system of claim 1, wherein:
   to determine the correspondence between the first and second vessel models, the at least one processor is further configured to:
      perform the projection pose estimation to estimate a geometric relationship comprising the one or more pose parameters between the first and second vessel models, so that the first and second vessel models are aligned with one another based on the geometric relationship.

4. The system of claim 3, wherein the one or more pose parameters comprise a translation parameter and a rotation parameter between the first and second vessel models.

5. The system of claim 3, wherein to determine the correspondence between the first and second vessel models, the at least one processor is further configured to:
   perform a point matching operation to match a first reference pattern of the vessel of interest in the first vessel model with a second reference pattern of the vessel of interest in the second vessel model.

6. The system of claim 5, wherein:
   the first reference pattern in the first vessel model comprises a centerline of the vessel of interest in the first vessel model; and
   the second reference pattern in the second vessel model comprises a centerline of the vessel of interest in the second vessel model.

7. The system of claim 5, wherein the first vessel model is a two-dimensional (2D) projection model, and the second vessel model is a three-dimensional (3D) model of the vessel of interest.

8. The system of claim 5, wherein:
   to determine the correspondence between the first and second vessel models, the at least one processor is further configured to:
      perform a longitudinal shift estimation to estimate a longitudinal relationship between the first and second vessel models, so that a longitudinal location of the first vessel model is aligned with a longitudinal location of the second vessel model based on the longitudinal relationship.

9. The system of claim 8, wherein to determine the correspondence between the first and second vessel models, the at least one processor is further configured to:
   perform a cross-sectional matching operation on the first and second vessel models.

10. The system of claim 9, wherein:
    the first vessel model is a two-dimensional (2D) cross-sectional model; and
    the second vessel model is a 2D projection model, a three-dimensional (3D) model, or another fused model generated from the 2D projection model and the 3D model.

11. The system of claim 1, wherein:
    each vessel model comprises at least one of a centerline, a radius, or a segmentation mask of the vessel of interest for a corresponding imaging modality.

12. The system of claim 1, wherein the plurality of imaging modalities comprise at least one of invasive X-ray angiography, 3-dimensional (3D) angiography, or intravascular imaging.

13. The system of claim 12, wherein:
    the 3D angiography comprises at least one of Computed Tomography Angiography (CTA) or Magnetic Resonance Angiography (MRA); and
    the intravascular imaging comprises at least one of Optical Coherence Tomography (OCT) or Intravascular Ultrasound (IVUS).

14. The system of claim 1, wherein to provide the diagnostic analysis result based on the fused model of the vessel of interest, the at least one processor is further configured to:
    perform a functional analysis based on the fused model to generate a Fractional Flow Reserve (FFR) or Wave-free Ratio (iFR) analysis result of the vessel of interest.

15. The system of claim 1, wherein the first vessel model comprises a two-dimensional (2D) model and the second vessel model comprises a three-dimensional (3D) model, and to provide the diagnostic analysis result based on the fused model of the vessel of interest, the at least one processor is further configured to:
    provide an improved 3D vessel reconstruction of the vessel of interest from the 3D model and vessel and lesion characteristics from the 2D model.

16. The system of claim 1, wherein to provide the diagnostic analysis result based on the fused model of the vessel of interest, the at least one processor is further configured to:
    provide an immersive visualization of the vessel of interest in augmented or virtual reality to visualize a structure of the vessel of interest and lesions of the vessel of interest.

17. The system of claim 1, wherein the one or more pose parameters provide a maximal mask overlap score between the first vessel structure in the first vessel model and the second vessel structure in the second vessel model, and performing the projection pose estimation to estimate the one or more pose parameters between the first and second vessel models comprises:

projecting a mask of the first vessel structure in the first vessel model into a view of the second vessel model, wherein the projected mask of the first vessel structure is overlapped with a mask of the second vessel structure in the second vessel model; and determining the one or more pose parameters that achieve the maximal mask overlap score between the projected mask of the first vessel structure and the mask of the second vessel structure in the second vessel model.

18. The system of claim 1, wherein the one or more pose parameters provide a maximal centerline closeness score, the first vessel structure comprises a centerline of the vessel of interest in the first vessel model, the second vessel structure comprises a centerline of the vessel of interest in the second vessel model, and performing the projection pose estimation to estimate the one or more pose parameters between the first and second vessel models comprises:

projecting the centerline of the vessel of interest in the first vessel model into a view of the second vessel model; and determining the one or more pose parameters that achieve the maximal centerline closeness score between the projected centerline of the vessel of interest in the first vessel model and the centerline of the vessel of interest in the second vessel model.

19. A computer-implemented method for multi-modality joint analysis of a plurality of vascular images, comprising:

receiving, at a communication interface, the plurality of vascular images acquired using a plurality of imaging modalities;

extracting, by at least one processor, a plurality of vessel models for a vessel of interest from the plurality of vascular images, wherein the plurality of vessel models are associated with the plurality of imaging modalities, respectively, wherein the plurality of vessel models comprise a first vessel model and a second vessel model;

determining, by the at least one processor, a correspondence among the plurality of vessel models at least by performing a projection pose estimation to estimate one or more pose parameters between the first and second vessel models, wherein the one or more pose parameters indicate an extent of matching between a first vessel structure in the first vessel model and a second vessel structure in the second vessel model;

fusing, by the at least one processor, the plurality of vessel models associated with the plurality of imaging modalities based on the correspondence to generate a fused model for the vessel of interest; and providing, by the at least one processor, a diagnostic analysis result based on the fused model of the vessel of interest.

20. A non-transitory computer-readable medium having a computer program stored thereon, wherein the computer program, when executed by at least one processor, performs a method for multi-modality joint analysis of a plurality of vascular images, the method comprising:

receiving the plurality of vascular images acquired using a plurality of imaging modalities;

extracting a plurality of vessel models for a vessel of interest from the plurality of vascular images, wherein the plurality of vessel models are associated with the plurality of imaging modalities, respectively, wherein the plurality of vessel models comprise a first vessel model and a second vessel model;

determining a correspondence among the plurality of vessel models at least by performing a projection pose estimation to estimate one or more pose parameters between the first and second vessel models, wherein the one or more pose parameters indicate an extent of matching between a first vessel structure in the first vessel model and a second vessel structure in the second vessel model;

fusing the plurality of vessel models associated with the plurality of imaging modalities based on the correspondence to generate a fused model for the vessel of interest; and providing a diagnostic analysis result based on the fused model of the vessel of interest.

* * * * *